US008866101B1

(12) United States Patent
Watanabe et al.

(10) Patent No.: US 8,866,101 B1
(45) Date of Patent: Oct. 21, 2014

(54) RADIATION IMAGE DETECTING DEVICE AND OPERATING METHOD THEREOF, AND RADIATION IMAGING SYSTEM

(71) Applicant: FUJIFILM Corporation, Tokyo (JP)

(72) Inventors: Keita Watanabe, Ashigarakami-gun (JP); Kentaro Noma, Ashigarakami-gun (JP); Yasufumi Oda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/229,128

(22) Filed: Mar. 28, 2014

(30) Foreign Application Priority Data

Mar. 29, 2013 (JP) .................................. 2013-073591
Mar. 19, 2014 (JP) .................................. 2014-057061

(51) Int. Cl.
*G01J 1/42* (2006.01)
*H01L 27/146* (2006.01)
*G01N 23/04* (2006.01)
*G01T 1/16* (2006.01)
*H04N 5/365* (2011.01)

(52) U.S. Cl.
CPC ...... *G01T 1/16* (2013.01); *G01N 23/04* (2013.01); *H04N 5/3655* (2013.01); *H04N 5/3658* (2013.01)
USPC .. 250/394; 250/395; 250/370.08; 250/370.09

(58) Field of Classification Search
CPC ........................... H04N 5/3658; H04N 5/3655
USPC ................ 250/394, 395, 370.08, 370.09
See application file for complete search history.

(56) References Cited

U.S. PATENT DOCUMENTS 8,249,322 B2 * 8/2012 Kuwabara et al. ............ 382/128
2009/0046917 A1 * 2/2009 Konishi ........................ 382/132

FOREIGN PATENT DOCUMENTS

JP 2011-254971 A 12/2011

* cited by examiner

*Primary Examiner* — David Porta
*Assistant Examiner* — Kenneth J Malkowski
(74) *Attorney, Agent, or Firm* — Birch, Stewart, Kolasch & Birch, LLP

(57) ABSTRACT

Binning readout reads out electric charge accumulated in pixels to signal lines in blocks of a plurality of adjoining pixel-rows. A correction image generator of a line defect corrector scales up an image size of a reference frame image RP outputted by the binning readout and corrects pixel values of the reference frame image RP, to produce a correction image RPC to be used for correction of a line defect occurring in an X-ray image XP. The scale-up is performed by applying row interpolation processing to the reference frame image RP. The correction of the pixel values is performed by multiplying the reference frame image RP after being subjected to the row interpolation processing by a correction coefficient. An adder adds the correction image RPC to the X-ray image XP, and produces an X-ray image XPC in which the line defect is corrected.

23 Claims, 20 Drawing Sheets

| BODY PART | TUBE VOLTAGE (kV) | TUBE CURRENT (mA) | EMISSION TIME |
|---|---|---|---|
| ⋮ | ⋮ | ⋮ | ⋮ |
| CHEST | V1 | I1 | T1 |
| ABDOMEN | V2 | I2 | T2 |
| ⋮ | ⋮ | ⋮ | ⋮ |

RADIATION IMAGE DETECTING DEVICE AND OPERATING METHOD THEREOF, AND RADIATION IMAGING SYSTEM

BACKGROUND OF THE INVENTION

1. Field of the Invention

The present invention relates to a radiation image detecting device having a line defect correction function for correcting a strip-shaped line defect occurring in a radiographic image, an operating method of the radiation image detecting device, and a radiation imaging system.

2. Description Related to the Prior Art

In a medical field, an X-ray imaging system using X-rays, as a kind of radiation, is known. The X-ray imaging system is constituted of an X-ray generating apparatus for generating the X-rays, and an X-ray imaging apparatus for taking an X-ray image of an object (a patient) by receiving the X-rays passed through the object. The X-ray generating apparatus includes an X-ray source for emitting the X-rays to the object, a source control unit for controlling the operation of the X-ray source, and an emission switch for inputting a command to actuate the X-ray source to the source control unit. The X-ray imaging apparatus includes an X-ray image detecting device for detecting the X-ray image that is produced from the X-rays passed through the object, and a console for controlling the operation of the X-ray image detecting device and storing and displaying the X-ray image.

A kind of the X-ray image detecting device using an image detector (a flat panel detector, FPD) that detects the X-ray image as an electric signal has become widespread. The image detector is constituted of a panel unit and a circuit unit. The panel unit has an image capturing field for capturing a radiographic image of the object. The panel unit has a plurality of pixels arranged in two dimensions and signal lines. The pixels each for accumulating electric charge produced in accordance with an X-ray amount incident thereon are arranged in a plurality of pixel-rows and pixel-columns. The electric charge is read out from the pixels through the signal lines on a pixel-row basis. Each pixel is provided with a photoelectric conversion element for producing and accumulating the electric charge, and a switching element such as a TFT (thin film transistor). The circuit unit includes a gate driver, a signal processing circuit, and a controller for controlling the operation of the panel unit through the gate driver and the signal processing circuit.

The gate driver issues gate pulses to drive the switching elements through scan lines provided on a pixel-row basis. The signal processing circuit outputs voltage in accordance with the electric charge read out through the signal lines provided on a pixel-column basis. The controller makes the panel unit perform three operations, that is, a pixel reset operation for discharging the electric charge accumulated in the pixels, an accumulation operation for accumulating the electric charge in the pixels by turning off the switching element of every pixel, and an image readout operation for reading out the electric charge from the first pixel-row to the last pixel-row on a pixel-row basis after the completion of the accumulation operation to capture an X-ray image of one frame (one screen) to a frame memory.

The pixel reset operation is an operation for removing dark charge accumulated in the pixels. The dark charge, which is based on dark current, becomes a noise component of the X-ray image, and hence the pixel reset operation is carried out. In the pixel reset operation, pixels are sequentially reset from the first pixel-row to the last pixel-row on a pixel-row basis, and after completing the reset of the last pixel-row, the reset is repeated again from the first pixel-row.

In order to appropriately take the X-ray image, the X-ray imaging apparatus requires information on the start of X-ray emission from the X-ray source. Japanese Patent Laid-Open Publication No. 2011-254971 discloses a communication method in which a signal related to the X-ray emission is communicated between the X-ray generating apparatus and the X-ray imaging apparatus, and a self-judgment method in which the X-ray image detecting device judges the start of the X-ray emission.

In the communication method, the X-ray image detecting device performs the pixel reset operation before the start of the X-ray emission. In the pixel reset operation, the electric charge accumulated in the pixels is read out and discharged on a pixel-row basis. If an emission start request is sent from the X-ray generating apparatus to the X-ray image detecting device during the pixel reset operation, the X-ray image detecting device permits the X-ray generating apparatus to start the X-ray emission at the time of completing the reset of the pixels of the last row. After the permission of the start of the X-ray emission, the X-ray image detecting device is shifted from the pixel reset operation to the accumulation operation.

In the self-judgment method, on the other hand, the start of the X-ray emission is judged by detecting variation of the signal due to the X-rays during the operation of the X-ray image detecting device. The X-ray image detecting device performs the accumulation operation between two types of readout operations, that is, a pre-emission readout operation for reading out the electric charge in predetermined cycles on a pixel-row basis and the image readout operation. If the X-ray emission is started during the pre-emission readout operation, the electric charge of each pixel rapidly increases and the signal varies largely, and thereby the start of the X-ray emission is detected. Upon detecting the start of the X-ray emission, the pre-emission readout operation is stopped and shifted to the accumulation operation. After a lapse of predetermined emission time, the image readout operation is carried out to sequentially read out the electric charge of the pixels from the first row on a pixel-row basis and produce the X-ray image based on the X-ray emission.

In the communication method, the accumulation operation is carried out and no electric charge is read out during the X-ray emission. According to the self-judgment method, on the other hand, in the duration between the start of the X-ray emission and the judgment of the emission start, the electric charge of a plurality of pixel-rows is read out by the pre-emission readout operation. Thus, not only the dark charge but also the electric charge produced by the X-ray emission is read out from the plurality of pixel-rows. This electric charge that is readout in advance is turned to be a deficit, and therefore a line of low density i.e. a line defect appears in the X-ray image.

According to the X-ray image detecting device described in the Japanese Patent Laid-Open Publication No. 2011-254971, the line defect is corrected based on a reference line image in which output of the electric charge read out sequentially in the pre-emission readout operation is recorded on a pixel-row basis. This X-ray image detecting device uses the reference line image for the judgment of the emission start too.

To be more specific, as shown in FIG. 18, in a standby state before the X-ray emission, the pre-emission readout operation is performed in which the gate driver sequentially issues gate pulses G(1) to G(N) (N is the number of the pixel-rows) at predetermined intervals H to read out the electric charge from the pixels of the first pixel-row to the last pixel-row on a pixel-row basis. Upon completing the reset of the last pixel-row, the readout is repeated from the first pixel-row. The output of the electric charge that is read out of the one pixel-row is recorded to the frame memory, as the reference line image.

By completing the readout of one frame, a reference frame image RP, which is composed of the reference line images of one frame, is recorded. A readout period of one frame is defined as one cycle. Upon completing the one cycle, the next cycle is started and the readout is repeated from the first pixel-row. Concurrently, the reference frame image RP is updated on a pixel-row basis using the reference line images of the next cycle.

In the judgment of the emission start, as shown in FIG. 19, a typical value of pixel values S of the reference line image sequentially outputted at the intervals H is compared with a predetermined judgment threshold value Th. As the typical value of the pixel values S of the reference line image to be compared with the judgment threshold value Th, a maximum value of the pixel values S of one pixel-row, or an average value or a sum value of the pixel values S of one pixel-row is used. As shown in an X-ray emission profile, which represents time-variation in an X-ray dose applied from the X-ray source per unit of time, the X-ray dose applied per unit of time is low immediately after the start of the X-ray emission, and is gradually increased to a set dose value determined in accordance with tube current. Round marks indicated with "E" represent the output timing of the reference line images. Letters "C", "C−1", and the like represent the pixel-rows from which the reference line images are outputted.

Before the start of the X-ray emission from the X-ray source, the pixel values S of the reference line image correspond to output according to the dark charge, and are much smaller than output according to the X-ray dose. Thus, the pixel value S according to the dark charge is regarded as a level of approximately zero in FIG. 19. After the start of the X-ray emission, the pixel values S of the reference line image are increased in accordance with the X-ray emission profile. After that, the typical value of the pixel values S exceeds the judgment threshold value Th. At the instant when the typical value of the pixel values S of the reference line image exceeds the judgment threshold value Th, the X-ray emission from the X-ray source is judged to be started.

As shown in FIG. 18, as soon as the X-ray emission is judged to be started, the controller immediately stops issuing the gate pulses and shifts the panel unit from the pre-emission readout operation to the accumulation operation. After a lapse of time determined in an imaging condition, the X-ray emission is expected to be completed, and the panel unit shifts to the image readout operation. The electric charge is read out on a pixel-row basis and an X-ray image XP is outputted. After the image readout operation, the panel unit shifts to the pre-emission readout operation again in a case where a reservation for the next imaging is made. The panel unit completes its operation in the case of no reservation for the next imaging.

FIGS. 18 and 19 show a state in which the typical value of the pixel values S of the reference line image of the Cth pixel-row exceeds the judgment threshold value Th, and hence the judgment of the emission start is made at the Cth pixel-row. However, the X-ray emission is actually started just moments before reading out the reference line image of the (C−2)th pixel-row, which is two pixel-rows previous to the Cth pixel-row (just moments before inputting the gate pulse (C−2) to the pixels of the (C−2)th pixel-row). Such a time delay between the start of the X-ray emission and the judgment of the emission start causes the readout of three pixel-rows, including the Cth pixel-row immediately before the stop of the pre-emission readout operation and the (C−1)th and (C−2)th pixel-rows being next previous to the Cth pixel-row, during the X-ray emission. This brings about the deficit in the electric charge.

Such a deficit in the electric charge manifests itself as a strip-shaped line defect extending in a pixel-row direction (X direction) in the X-ray image XP, as shown in FIG. 20. In the drawing, a right graph shows a plot of pixel values D of an arbitrary column X (X=1 to M, M is the number of the pixel-columns) in the X-ray image XP along a pixel-column direction (Y direction). The pixel value D begins decreasing from the (C−2)th pixel-row at which the pre-emission readout operation is performed just moments after the start of the X-ray emission, and comes to the lowest at the Cth pixel-row at which the judgment of the emission start is made and just moments before stopping the pre-emission readout operation. Accordingly, the line defect becomes severer in a stepwise manner from the (C−2)th pixel-row to the Cth pixel-row, and the severest at the Cth pixel-row. A difference in density is conspicuous between the Cth pixel-row and the next (C+1)th pixel-row, due to a difference in the pixel values D. Note that, the plot does not show an effect of attenuation of the X-rays by the object and an offset of the dark charge (the same goes for FIG. 21).

As shown in FIG. 21, the reference frame image RP represents the offset caused by the dark charge of the pixels before the X-ray emission. However, the reference line images of the three pixel-rows, i.e. from the (C−2)th pixel-row at which the pre-emission readout operation is firstly performed after the start of the X-ray emission to the Cth pixel-row at which the judgment of the emission start is made and just moments before the stop of the pre-emission readout operation, represent output according to the X-ray dose and correspond to the line defect in the X-ray image XP.

The pixel values S of the reference line images of the three pixel-rows corresponding to the line defect are increased in a stepwise manner from the (C−2)th pixel-row to the Cth pixel-row, oppositely to the line defect in the X-ray image XP. In FIG. 21, a right graph shows a plot of pixel values S of the arbitrary pixel-column X in the reference frame image RP along the Y direction, just as with the plot of FIG. 20. The pixel values S of the reference frame image RP are approximately zero from the first pixel-row to the (C−3)th pixel-row before the start of the X-ray emission. The pixel value S begins increasing from the (C−2)th pixel-row, and comes to the highest at the Cth pixel-row. The typical value of the pixel values S exceeds the judgment threshold value Th at the Cth pixel-row. The pixel values S of the (C+1)th pixel-row to the Nth pixel-row are obtained in the pre-emission readout operation of the previous cycle, and are approximately zero just as with the pixel values S of the first to (C−3)th pixel-rows.

The difference in the pixel value D of the X-ray image XP between the Cth pixel-row just moments before stopping the pre-emission readout operation and the next (C+1)th pixel-row becomes maximum, as for the difference in the pixel value D between adjoining two pixel-rows of the pixel-rows corresponding to the line defect of the X-ray image XP. This difference is called a difference amount. Representing an absolute value of the difference amount as AD (see FIG. 20), the difference amount AD is equal to a pixel value SQ (see FIG. 21) of the Cth pixel-row in the reference frame image RP. Furthermore, a falling gradient of the pixel value D from the (C−2)th pixel-row to the Cth pixel-row in the X-ray image XP coincides with a rising gradient of the pixel value S from the (C−2)th pixel-row to the Cth pixel-row in the reference frame image RP. In other words, the complementary relation holds between the pixel values D of the pixel-rows having the line defect in the X-ray image XP and the pixel values S of the pixel-rows corresponding to the line defect in the reference frame image RP. Therefore, in the Japanese Patent Laid-Open Publication No. 2011-254971, the reference frame image RP is used as a correction image for correcting the line defect. The line defect of the X-ray image XP is corrected by adding the pixel values S of the pixel-rows corresponding to the line defect in the reference frame image RP to the pixel values D of the pixel-rows having the line defect in the X-ray image XP.

By the way, according to another method of the readout operation, gate pulses are concurrently inputted to a plurality of adjoining pixel-rows and the electric charge accumulated in the pixels is discharged from the plurality of pixel-rows at a time to the signal lines, in order to shorten time required for the one cycle. In reading out the electric charge from the plurality of adjoining pixel-rows at a time, the electric charge of the pixels of the plural pixel-rows is added in each signal line on a pixel-column basis. Such a readout operation by which the electric charge is readout from the plurality of pixel-rows in a state of addition is called binning readout. Also, the plurality of adjoining pixel-rows from which the electric charge is read out at a time is called a binning pixel-row. The binning readout can shorten time required for the one cycle of the readout from the first row to the last row, as compared with the case of the readout on a pixel-row basis, and hence facilitates reducing the dark charge accumulated in the pixels.

However, in the case of performing the binning readout as the pre-emission readout operation, there is a problem that the line defect of the X-ray image XP cannot be corrected in the method described above, that is, by simply adding the pixel values S of the reference frame image RP to the pixel values D of the X-ray image XP.

This is because in the binning readout, the electric charge is discharged at a time from the pixels of the plurality of pixel-rows composing one binning pixel-row. Thus, the reference line image is composed of values each of which corresponds to the electric charge of the plurality of pixels, for example, four pixels, outputted in a state of being added on a column-by-column basis. Sequentially recording the reference line images on a binning pixel-row basis allows obtainment of the reference frame image RP. On the other hand, the X-ray image XP is read out on a pixel-row basis. Thus, the pixel value SQ of the reference frame image RP recorded by the binning readout at a part corresponding to the line defect is larger than the difference amount $\Delta D$ in the X-ray image XP at a part of the line defect, and the values do not coincide each other. In the reference frame image RP recorded by the binning readout, since the one binning pixel-row is composed of the plurality of pixel-rows, the number of the binning pixel-rows of the reference frame image RP is less than the number of the pixel-rows of the X-ray image XP. Setting the four pixel-rows as the one binning pixel-row, for example, the number of the binning pixel-rows of the reference frame image RP is a quarter of the number of the pixel-rows of the X-ray image XP. Thus, the reference frame image RP recorded in the binning readout is of the same image size as the X-ray image XP in the pixel-row direction, and of smaller image size in the pixel-column direction. Therefore, the complementary relation between the pixel values D of the pixel-rows having the line defect in the X-ray image XP and the pixel values S of the pixel-rows corresponding to the line defect of the reference frame image RP does not hold true. Therefore, the line defect of the X-ray image XP cannot be corrected by simply adding the reference frame image RP to the X-ray image XP, as described in the Japanese Patent Laid-Open Publication No. 2011-254971.

SUMMARY OF THE INVENTION

An object of the present invention is to provide a radiation image detecting device, an operating method thereof, and a radiation imaging system that can correct a line defect of a radiographic image with the use of reference line images recorded by binning readout.

To achieve the above and other objects, a radiation image detecting device according to the present invention includes a panel unit, a plurality of pixels, a plurality of scan lines, a signal line, a controller, a reference line image record controller, an emission start judging unit, a correction image generator, and a line defect corrector. The panel unit has an image capturing field for imaging a radiographic image of an object by receiving radiation emitted from a radiation source. The plurality of pixels are arranged in the panel unit in a two-dimensional array having a plurality of pixel-rows and a pixel-column. Each of the pixels produces and accumulates electric charge. The plurality of scan lines are provided in the panel unit on a pixel-row basis, and makes the pixel-row having the pixels from which the electric charge is to be read out in an ON state. The signal line is provided in the panel unit on a pixel-column basis, for reading out the electric charge from the pixels on a pixel-column basis. The controller controls the panel unit to perform three types of operations of a pre-emission readout operation, an accumulation operation, and an image readout operation. In the pre-emission readout operation, a plurality of adjoining pixel-rows are set as a binning pixel-row. Binning readout of the electric charge is performed on a binning pixel-row basis sequentially from a first binning pixel-row to a last binning pixel-row and repeated from the first binning pixel-row upon reaching the last binning pixel-row, in order to obtain reference line images each having a pixel value being a sum of the electric charge of a plurality of pixels in a same pixel-column. The accumulation operation is performed instead of the pre-emission readout operation, in a case where the radiation source starts emitting the radiation while the binning readout of the electric charge is repeated on a binning pixel-row basis, for accumulating the electric charge in the pixels in accordance with the radiation. The image readout operation is started after completion of emission of the radiation from the radiation source, for reading out the electric charge from the pixels on a pixel-row basis and converting the electric charge to pixel values for forming the radiographic image. The reference line image record controller obtains the reference line images of a plurality of binning pixel-rows by sequentially recording the reference line images to a memory whenever performing the binning readout. The emission start judging unit judges the start of emission of the radiation from the radiation source. The correction image generator produces a correction image used for correcting a strip-shape line defect occurring in a pixel-row direction of the radiographic image due to a time delay between the start of emission of the radiation and a judgment of the start of emission, by scaling up an image size of the reference line images of the plurality of binning pixel-rows in a pixel-column direction and correcting the pixel values. The line defect corrector corrects the line defect by adding the correction image to the radiographic image.

The correction image generator preferably corrects the pixel value of the reference line image based on an immediately-preceding reference line image that is obtained immediately before stopping the pre-emission readout operation, out of the reference line images of the plurality of binning pixel-rows.

The correction image generator preferably includes a correction coefficient calculator for calculating a correction coefficient used for converting the pixel value of the reference line image to a value corresponding to a pixel value of the radiographic image; and a pixel value corrector for multiplying the pixel value of the reference line image by the correction coefficient calculated by the correction coefficient calculator.

The correction coefficient calculator may calculate a ratio $\Delta D/SQ$ as the correction coefficient. SQ represents a pixel value of the immediately-preceding reference line image. $\Delta D$ represents a difference amount being a maximum value of difference in a pixel value D of the radiographic image between adjoining two of the pixel-rows caused by the line defect.

The correction coefficient calculator may calculate a ratio $\Delta DR/SQR$ as the correction coefficient. SQR represents a typical value of a pixel value SQ of the immediately-preceding reference line image. $\Delta DR$ represents a typical value of a difference amount $\Delta D$ being a maximum value of difference in a pixel value D of the radiographic image between adjoining two of the pixel-rows caused by the line defect.

The typical value SQR may be an average SQave of the pixel values SQ, and the typical value $\Delta DR$ may be an average $\Delta D$ave of the difference amounts $\Delta D$.

The correction coefficient calculator preferably calculates the average SQave and the average $\Delta D$ave with excluding a pixel value of a defect pixel from the pixel values SQ and the pixel values D that are used for calculation of the average SQave and the average $\Delta D$ave.

The typical value SQR may be a median value SQC of the pixel values SQ, and the typical value $\Delta DR$ may be a median value $\Delta DC$ of the difference amounts $\Delta D$.

The correction coefficient calculator may calculate a reciprocal of a number of the pixel-rows composing the binning pixel-row, as the correction coefficient.

The correction image generator preferably extracts the immediately-preceding reference line image and a plurality of the reference line images next to the immediately-preceding reference line image as line-defect-corresponding reference line images, out of the reference line images of the plurality of binning pixel-rows, and produces the correction image based on the line-defect-corresponding reference line images alone.

The pixel value corrector may uniformly multiply the pixel values of the line-defect-corresponding reference line images by the correction coefficient calculated by the correction coefficient calculator.

It is preferable that the radiation image detecting device further includes a correction coefficient modifier for modifying the correction coefficient calculated by the correction coefficient calculator to a correction coefficient specific to the line-defect-corresponding reference line image other than the immediately-preceding reference line image. The pixel value corrector multiplies a pixel value of the immediately-preceding reference line image by the correction coefficient calculated by the correction coefficient calculator, and multiplies a pixel value of the line-defect-corresponding reference line image other than the immediately-preceding reference line image by the correction coefficient modified by the correction coefficient modifier.

The correction image generator preferably scales up an image size of the reference line images of the plurality of binning pixel-rows in the pixel-column direction by row interpolation processing.

The row interpolation processing may apply linear interpolation or spline interpolation between the reference line images next to each other.

The reference line images of the plurality of binning pixel-rows may coincide with the reference line images of one frame extending from the first binning pixel-row to the last binning pixel-row.

In a case where the pre-emission readout operation of one frame extending from the first binning pixel-row to the last binning pixel-row is set as one cycle, the reference line image record controller preferably sequentially updates the reference line images of one frame obtained in the pre-emission readout operation of an Sk-th cycle with the reference line images obtained in the pre-emission readout operation of an (Sk+1)-th cycle on a binning pixel-row basis.

The emission start judging unit preferably judges the start of emission of the radiation based on the reference line images.

The radiation image detecting device may further include a leak corrector for subtracting a pixel value based on leak current leaking from the pixel according to application of the radiation from a pixel value of the reference line image, before the correction image generator generates the correction image.

The controller may also function as the reference line image record controller. The controller may also function as the line defect corrector. The line defect corrector may also function as the correction image generator.

An operating method of a radiation image detecting device includes the steps of performing the pre-emission readout operation, until the emission start judging unit judges the start of emission; in the pre-emission readout operation, setting a plurality of adjoining pixel-rows as a binning pixel-row, and performing binning readout of the electric charge on a binning pixel-row basis sequentially from a first binning pixel-row to a last binning pixel-row and repeating the binning readout from the first binning pixel-row upon reaching the last binning pixel-row, in order to obtain reference line images each having a pixel value being a sum of the electric charge of a plurality of pixels in a same pixel-column; judging the start of emission by the emission start judging unit, while the binning readout of the electric charge is repeated on a binning pixel-row basis; performing the accumulation operation instead of the pre-emission readout operation, when the emission start judgment unit judges the start of emission; performing the image readout operation after completion of emission of the radiation from the radiation source; producing by a correction image generator a correction image used for correcting a strip-shape line defect occurring in a pixel-row direction of the radiographic image due to a time delay between the start of emission of the radiation and the judgment of the start of emission, by scaling up an image size of the reference line images of a plurality of binning pixel-rows in a pixel-column direction and correcting the pixel values; and correcting the line defect by a line defect corrector by adding the correction image to the radiographic image.

A radiation imaging system according to the present invention includes a radiation image detecting device for detecting a radiographic image of an object by receiving radiation emitted from a radiation source, and a line defect correction device for correcting a strip-shape line defect occurring in the radiographic image.

According to the present invention, the correction image, which is to be used for correcting the line defect occurring in the radiographic image, is produced by applying the scale-up of the image size and the correction of the pixel values to the reference line images recorded by the binning readout. Thus, it is possible to provide the radiation image detecting device that can correct the line defect in the radiographic image by using the reference line images recorded by the binning readout.

BRIEF DESCRIPTION OF DRAWINGS

For more complete understanding of the present invention, and the advantage thereof, reference is now made to the subsequent descriptions taken in conjunction with the accompanying drawings, in which.

DESCRIPTION OF THE PREFERRED EMBODIMENTS

First Embodiment

Figure 1:
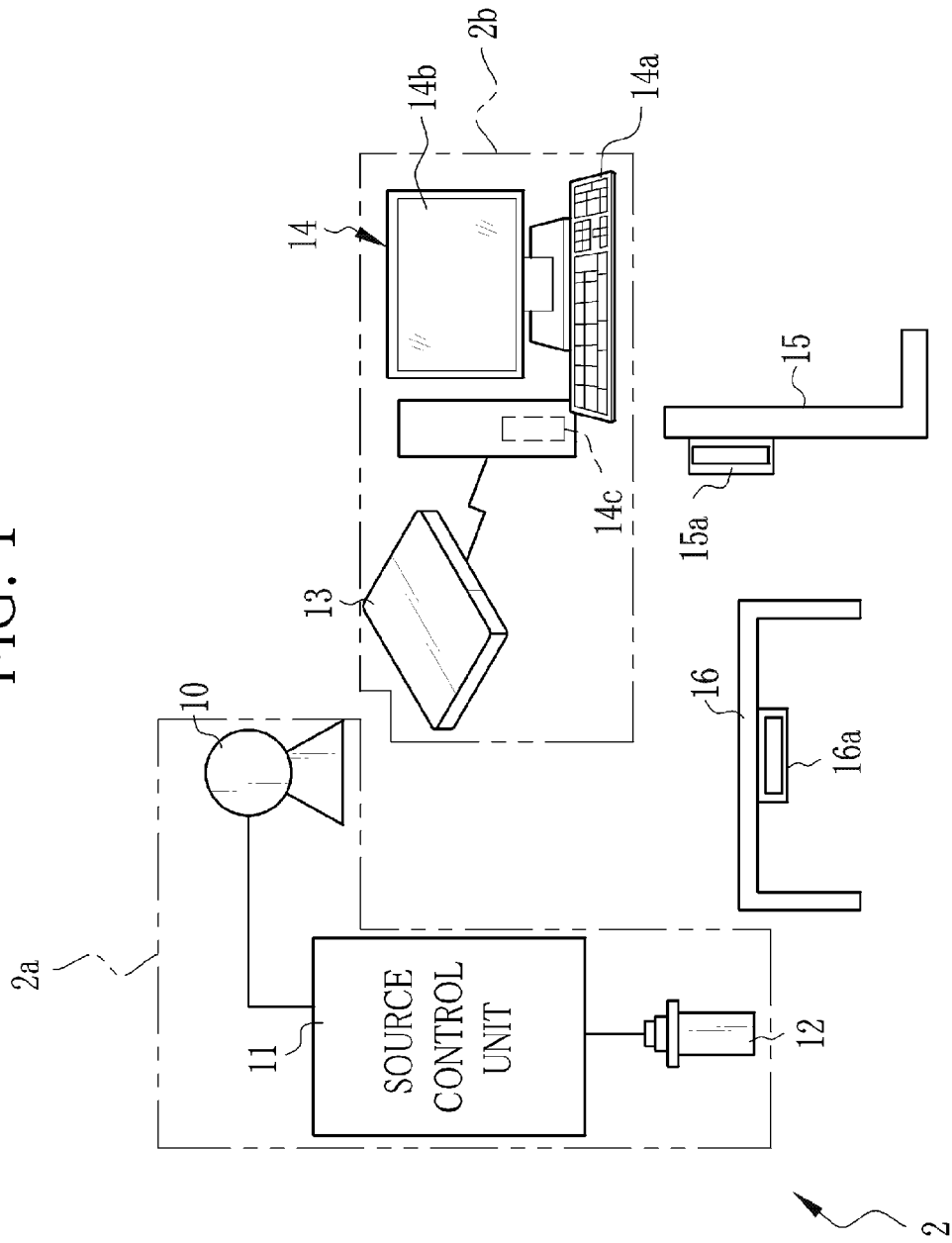
FIG. 1 is a schematic view of an X-ray imaging system.

In FIG. 1, an X-ray imaging system 2 is constituted of an X-ray generating apparatus 2a and an X-ray imaging appa-ratus 2b. The X-ray generating apparatus 2a includes an X-ray source 10, a source control unit 11 for controlling the operation of the X-ray source 10, and an emission switch 12 for commanding the X-ray source 10 to start a warm-up and an X-ray emission. The X-ray imaging apparatus 2b, being a portable X-ray image detecting device, includes an electronic cassette 13 and a console 14 that is in charge of operation control of the electronic cassette 13 and display processing of an X-ray image. In addition, the X-ray imaging system 2 is provided with an imaging stand 15 for imaging an object in a standing position, an imaging table 16 for imaging the object in a lying position, and a source shift device (not shown) for setting the X-ray source 10 in a desired orientation and position. The source shift device shifts the X-ray source 10 so as to be opposed to the imaging stand 15 or the imaging table 16.

No electric connection is established between the X-ray generating apparatus 2a and the X-ray imaging apparatus 2b, and therefore no synchronization signal for synchronizing the X-ray generating apparatus 2a and the X-ray imaging apparatus 2b is communicated therebetween. However, the electronic cassette 13 has the function of making a judgment of a emission start i.e. judging whether or not the X-ray emission has been started. Thereby, it is possible to synchronize the operation of the electronic cassette 13 to the start of the X-ray emission by the X-ray generating apparatus 2a.

As is widely known, the X-ray source 10 has an X-ray tube and an irradiation field limiter (collimator) for limiting an irradiation field of the X-rays radiating from the X-ray tube. The X-ray tube has a cathode being a filament for emitting thermoelectrons, and an anode (target) that radiates the X-rays by collision of the thermoelectrons emitted from the cathode. In response to a warm-up start command, the filament is preheated and the anode starts rotating. The warm-up is completed when the preheat of the filament is completed and the RPM of the anode reaches a predetermined value. The irradiation field limiter is composed of, for example, four lead plates for blocking the X-rays. The four lead plates are disposed in each side of a rectangle so as to form a rectangular irradiation opening in a middle to pass the X-rays therethrough. Shifting the position of the lead plates varies the size of the irradiation opening to limit the irradiation field.

The console 14 is coomunicatably connected to the electronic cassette 13 by a wired or wireless method. The console 14 controls the operation of the electronic cassette 13 in response to input by an operator such as a radiological technician from an input device 14a such as a keyboard. An X-ray image from the electronic cassette 13 is displayed on a display 14b of the console 14. Data of the X-ray image is stored to a storage device 14c including a hard disk and a memory of the console 14, an image storage server connected to the console 14 through a network, or the like.

The console 14 receives input of an examination order including information about sex and age of an object, a body part to be imaged, an examination purpose, and the like and displays the examination order on the display 14b. The examination order is inputted from an external system e.g. a HIS (hospital information system) or a RIS (radiography information system) that manages object data and examination data related to radiography, or inputted manually by the operator. The examination order includes an item of the body part to be imaged e.g. a head, a chest, an abdomen, a hand, fingers, and the like. The operator confirms the contents of the examination order on the display 14b, and inputs an imaging condition corresponding to the contents through an operation screen on the display 14b.

Figures 2, 3:
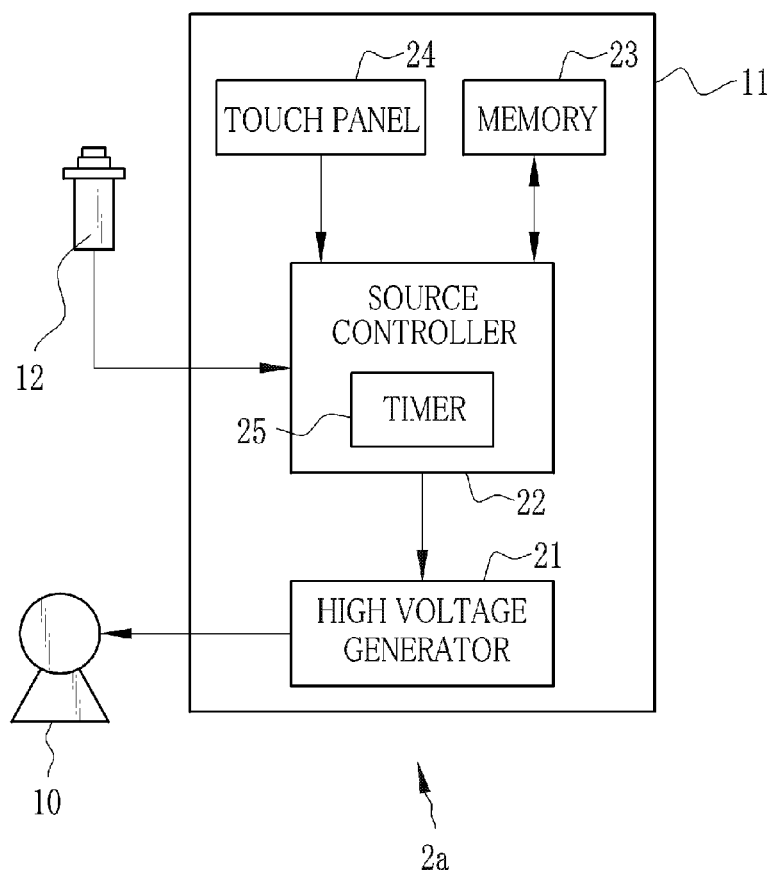
FIG. 2 is a drawing of an imaging condition table.
FIG. 3 is a block diagram of a source control unit.

In FIG. 2, the storage device 14c stores an imaging condition table 20. The imaging condition includes information about the object such as the body part to be imaged, the sex of the object, the age of the object, and a body thickness of the object, and an emission condition of the X-rays from the X-ray source 10. The emission condition is determined in consideration of the information about the body part and the object. The emission condition includes tube voltage (in units of kV) for determining an energy spectrum of the X-rays emitted from the X-ray source 10, tube current (in units of mA) for determining an emission dose per unit of time, and emission time (in units of s) of the X-rays.

The imaging condition table 20 stores the correlation between the body part to be imaged including the chest, the abdomen, and the like and the emission condition corresponding to the body part. By choosing the body part, the emission condition corresponding to the body part is read out. Each value of the emission condition (the tube voltage, the tube current, and the emission time) read out of the imaging condition table 20 can be finely adjusted in accordance with the sex, the age, and the body thickness of the object. The tube current and the emission time are recorded independently in the imaging condition table 20 of this embodiment. However, since a total emission dose depends on the product of the tube current and the emission time, a value of a tube current-time product (mAs value), being the product of the tube current and the emission time, may be recorded instead.

In FIG. 3, the source control unit 11 is provided with a high voltage generator 21 that generates the high tube voltage by multiplying input voltage using a transformer and supplies the high tube voltage to the X-ray source 10 through a high voltage cable, a source controller 22 that controls the tube voltage and the tube current to be applied to the X-ray source 10 and the emission time of the X-rays, a memory 23, and a touch panel 24.

To the source controller 22, the emission switch 12, the high voltage generator 21, the memory 23, and the touch panel 24 are connected. The emission switch 12 is a two-step press switch for inputting commands to the source controller 22. Upon a first-step press (half push) of the emission switch 12, the source controller 22 issues a warm-up command signal to the high voltage generator 21 to start warming up the X-ray source 10. Upon a second-step press (full push) of the emission switch 12, the source controller 22 issues an emission command signal to the high voltage generator 21 to start an X-ray emission from the X-ray source 10.

The memory 23 stores in advance a plurality of types of imaging conditions including the emission conditions such as the tube voltage, the tube current, and the emission time, as with the storage device 14c of the console 14. The imaging condition is set manually by the operator through the touch panel 24. The plurality of types of imaging conditions are readout of the memory 23 and displayed on the touch panel 24. The operator chooses the same imaging condition as that inputted to the console 14 out of the imaging conditions read out of the memory 24, and thereby the imaging condition is set in the source control unit 11. As in the case of the console 14, each value of the imaging condition is finely adjustable. The source controller 22 contains a timer 25 in order to stop the X-ray emission when the set emission time has elapsed.

Figure 4:
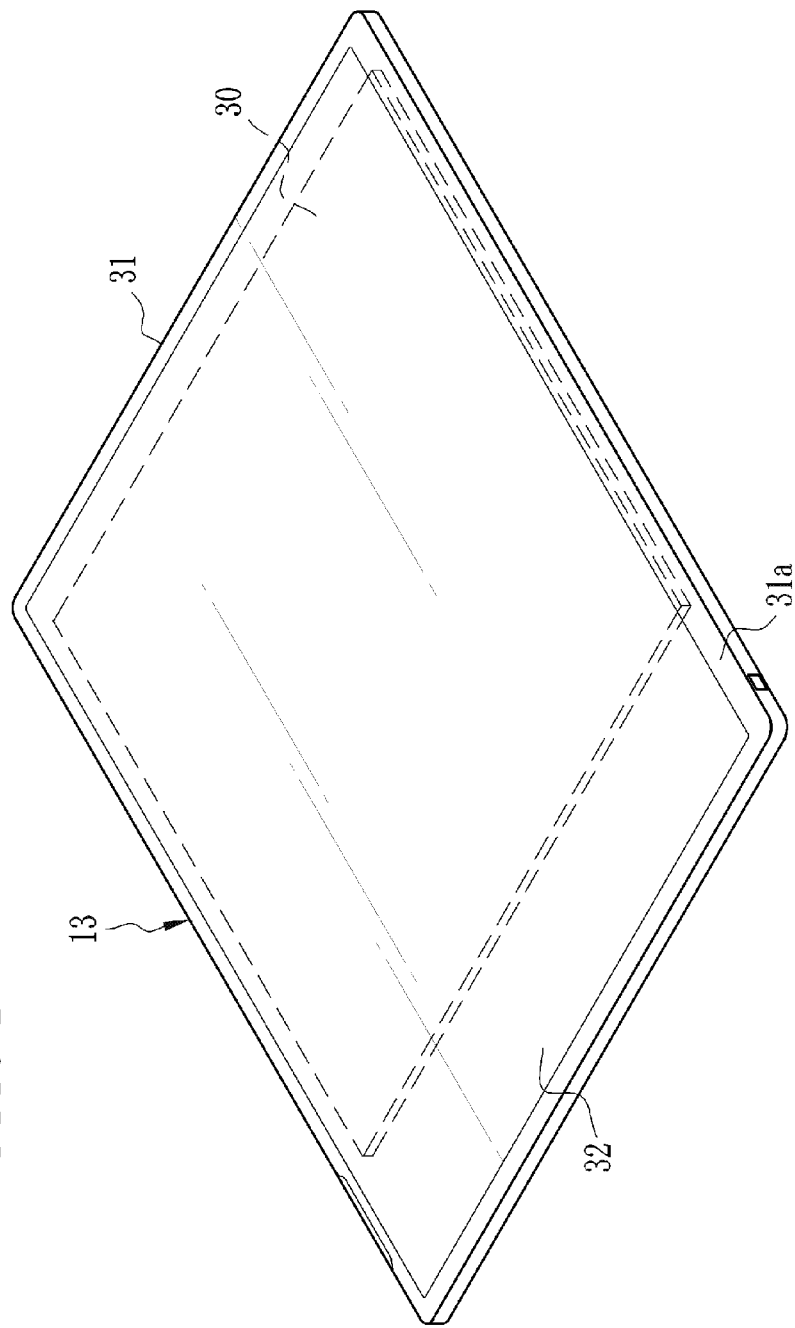
FIG. 4 is a perspective view of an electronic cassette.

In FIG. 4, the electronic cassette 13, which detects the X-rays passed through the object and outputs the X-ray image, is composed of an image detector 30 and a flat box-shaped portable housing 31 containing the image detector 30. The housing 31 is made of a conductive resin, for example. The housing 31 has a rectangular opening at its front surface 31a on which the X-rays are incident. A X-ray transparent plate 32 being a top plate is fitted into the opening. The X-ray transparent plate 32 is made of a carbon material possessing light weight, high stiffness, and high X-ray transmittance. The housing 31 also functions as an electromagnetic shield, which prevents entry of electromagnetic noise to the electronic cassette 13 and radiation of electromagnetic noise from the electronic cassette 13 to the outside. In addition to the image detector 30, the housing 31 contains a battery (secondary battery) for supplying electric power to drive the electronic cassette 13 and an antenna for establishing wireless communication of data such as the X-ray image with the console 14.

The housing 31 is of a size compatible with the International Standard ISO4090:2001, as with the film cassette and the IP cassette. The electronic cassette 13 is detachably loaded in a holder 15a, 16a (see FIG. 1) of the imaging stand 15 or the imaging table 16 in such a position that the front surface 31a of the housing 31 is opposed to the X-ray source 10. The source shift device shifts the X-ray source 10 depending on which one of the imaging stand 15 and the imaging table 16 to use.

The electronic cassette 13 can be used by itself, instead of being loaded in the imaging stand 15 or the imaging table 16, in a state of being put on a bed under the object lying or held by the object himself/herself. Furthermore, the electronic cassette 13 is approximately of the same size as the film cassette and the IP cassette, and is loadable in an existing imaging stand or table designed for the film cassette and the IP cassette. Note that, the housing 31 may not be of the size compatible with the International Standard ISO4090:2001.

Figure 5:
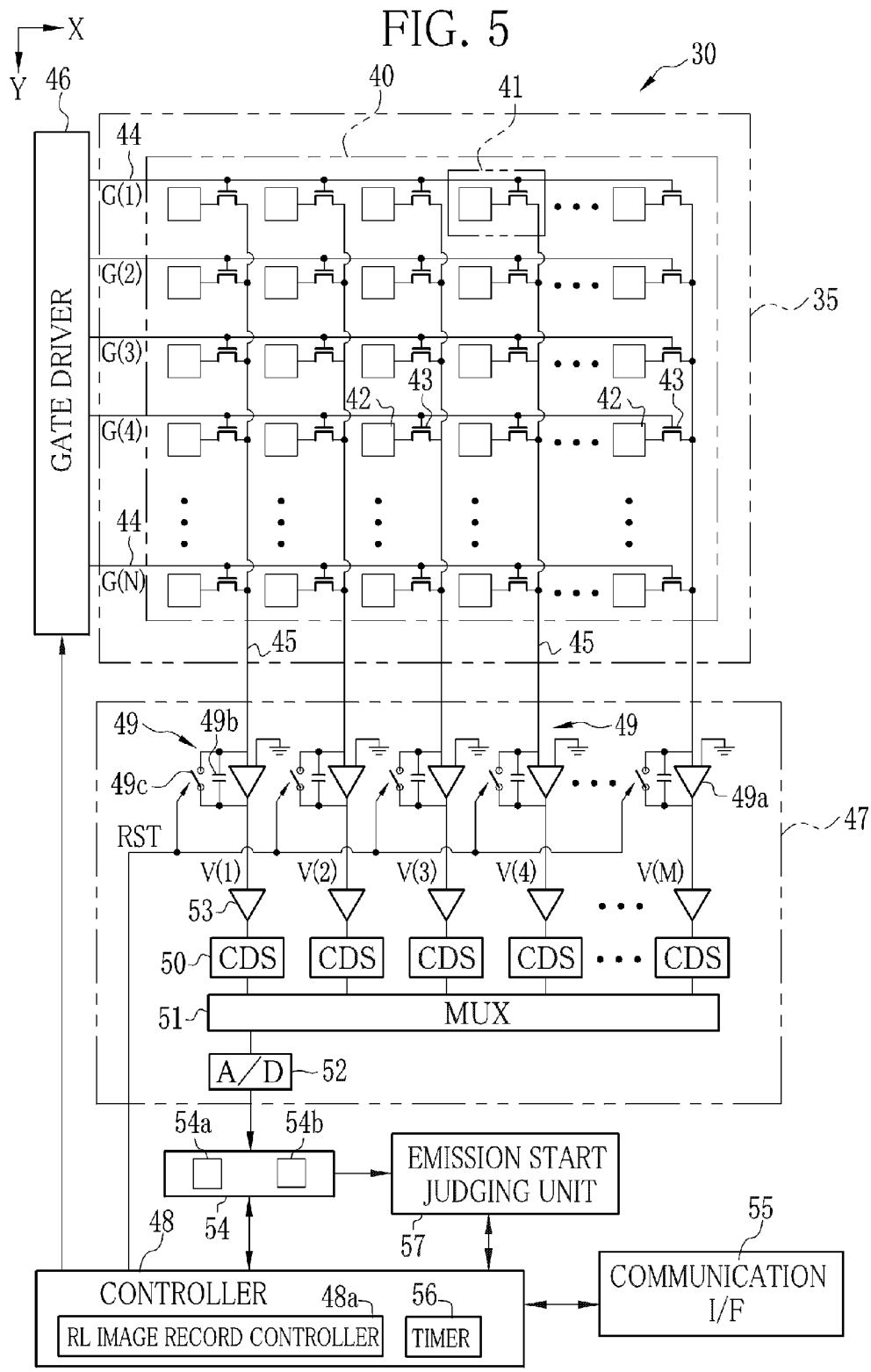
FIG. 5 is a block diagram of an image detector.

In FIG. 5, the image detector 30 is constituted of a panel unit 35 and a circuit unit for controlling the operation of the panel unit 35. The panel unit 35 has a TFT active matrix substrate and an image capturing field 40 formed in the substrate. In the image capturing field 40, a plurality of pixels 41 each for accumulating electric charge in accordance with an X-ray dose incident thereon are arranged into a matrix of N pixel-rows (Y direction) by M pixel-columns (X direction) at a predetermined pitch. N and M are integers of 2 or more, and N, M≈2000, for example. Note that, the pixels 41 may not be in a rectangular matrix array, but in a honeycomb array.

The panel unit 35 is of an indirect conversion type, having a scintillator (phosphor, not shown) for converting the X-rays into visible light. The pixels 41 perform photoelectric conversion of the visible light converted by the scintillator. The scintillator is made of CsI:Tl (thallium activated cesium iodide), GOS (Gd2O2S:Tb, terbium activated gadolinium oxysulfide), or the like, and is opposed to the entire image capturing field 40 having the matrix of pixels 41. Note that, the scintillator and the active matrix substrate may be disposed in either a PSS (penetration side sampling) method in which the scintillator and the substrate are disposed in this order from an X-ray incident side, or an ISS (irradiation side sampling) method in which the substrate and the scintillator are disposed in this order, oppositely to the PSS method. Also, a panel unit of a direct conversion type, which has a conversion layer (amorphous selenium or the like) for directly converting the X-rays into the electric charge without using the scintillator, may be used instead.

As is widely known, the pixel 41 is composed of a photoelectric conversion element 42 that produces the electric charge (electron and hole pairs) upon incidence of the visible light and accumulates the electric charge, and a TFT 43 being a switching element.

The photoelectric conversion element 42 has a semiconducting layer (of PIN (p-intrinsic-n) type, for example) for producing the electric charge, and an upper electrode and a lower electrode disposed on the top and bottom of the semiconducting layer. The lower electrode of the photoelectric conversion element 42 is connected to the TFT 43, and the upper electrode of the photoelectric conversion element 42 is connected to a bias line. There are a same number of bias lines provided as the number (N pixel-rows) of the pixel-rows of the pixels 41. All the bias lines are coupled to a bus. The bus is connected to a bias power supply. A bias voltage is applied from the bias power supply to the upper electrodes of the photoelectric conversion elements 42 through the bus and the bias lines. Since the application of the bias voltage produces an electric field in the semiconducting layer, the electric charge (electron and hole pairs) produced in the semiconducting layer by the photoelectric conversion is attracted to the upper and lower electrodes, one of which has a positive polarity and the other of which has a negative polarity. Thereby, the electric charge is accumulated in the photoelectric conversion element 42.

A gate electrode of the TFT 43 is connected to a scan line 44, a source electrode thereof is connected to s signal line 45, and a drain electrode thereof is connected to the photoelectric conversion element 42. The scan lines 44 and the signal lines 45 are routed into a lattice in the image capturing field 40. The number of the scan lines 44 coincides with the number (N pixel-rows) of the pixel-rows of the pixels 41, and the pixels 41 of one pixel-row are connected to the common scan line 44. The number of the signal lines 45 coincides with the number (M pixel-columns) of the columns of the pixels 41, and the pixels 41 of one pixel-column are connected to the common signal line 45. All the scan lines 44 are connected to the gate driver 46. All the signal lines 45 are connected to a signal processing circuit 47.

The circuit unit for controlling the operation of the panel unit 35 includes the gate driver 46, the signal processing circuit 47, a controller 48, and the like. The gate driver 46 outputs a gate pulse G to the gate electrodes of the TFTs 43 of the same pixel-row through the scan line 44, to switch the TFTs 43 between an ON state and an OFF state. A duration of the ON state of the TFT 43 is defined by a pulse width of the gate pulse G. After a lapse of time defined by the pulse width, the TFT 43 returns to the OFF state. In the ON state of the TFT 43, the electric charge accumulated in the photoelectric conversion element 42 of the pixel 41 is inputted to the signal processing circuit 47 through the signal line 45. The controller 48 makes the panel unit 35 perform a pre-emission readout operation, an accumulation operation, and an image readout operation. In the pre-emission readout operation, the electric charge accumulated in the pixels 41 before the X-ray emission is read out and recorded to a frame memory 54 through the signal processing circuit 47. In the accumulation operation, the electric charge is accumulated in accordance with the X-ray dose incident thereon. In the image readout operation, the electric charge accumulated in the pixels 41 are read out after the completion of the X-ray emission, and recorded to the frame memory 54 through the signal processing circuit 47.

The signal processing circuit 47 includes integrators 49, correlated double sampling circuits (CDSs) 50, a multiplexer (MUX) 51, an analog-to-digital converter (A/D) 52, and the like. The integrator 49 is connected to each signal line 45 on a one-by-one basis. The integrator 49 is composed of an operational amplifier 49a and a capacitor 49b connected between input and output terminals of the operational amplifier 49a. The signal line 45 is connected to one of the input terminals of the operational amplifier 49a. The other input terminal of the operational amplifier 49a is connected to a ground (GND). A reset switch 49c is connected in parallel to the capacitor 49b. The integrator 49 integrates the electric charge inputted from the signal line 45. Then, the integrators 49 convert the integrated electric charge into analog voltage signals V(1) to V(M), and output the voltage signals V(1) to V(M).

The output terminal of the operational amplifier 49a of each pixel-column is connected to the MUX 51 through an amplifier 53 and the CDS 50. Output of the MUX 51 is connected to the A/D 52. The CDS 50 has sample holder circuits. The CDS 50 applies correlation double sampling to an output voltage signal of the integrator 49 to remove a reset noise component of the integrator 49, and holds (sample holds) the voltage signal outputted from the integrator 49 for a predetermined time period in its sample hold circuit. The MUX 51 sequentially selects one of the CDSs 50 connected in parallel by an electronic switch based on an operation control signal from a shift resistor (not shown), and inputs the voltage signals V(1) to V(M) outputted from the selected CDSs 50 in series to the A/D 52. Note that, another amplifier may be connected between the MUX 51 and the A/D 52.

The A/D 52 converts the inputted analog voltage signals V(1) to V(M) of one pixel-row into digital values (pixel values), and outputs the pixel values to the frame memory 54 contained in the electronic cassette 13. The frame memory 54 stores the pixel values of the one pixel-row that are read out at a time with being associated with coordinates of individual pixels 41.

As soon as the MUX 51 reads out the voltage signals V(1) to V(M) of one pixel-row from the integrators 49, the controller 48 outputs an amplifier reset pulse RST to the integrators 49 to turn on the reset switches 49c. Thereby, the electric charge of the one pixel-row accumulated in the capacitors 49b is discharged and the integrators 49 are reset. After the reset of the integrators 49, the reset switches 49c are turned off again as a preparation to readout of the next pixel-row.

The frame memory 54 has a first storage area 54a for recording an X-ray image XP (see FIGS. 6 and 9) obtained in the image readout operation, and a second storage area 54b for recording a reference frame image RP (see FIGS. 6 and 10) obtained in the pre-emission readout operation.

The communication I/F 55 is wiredly or wirelessly connected to the console 14 to mediate transmission and reception of information to and from the console 14. The communication I/F 55 receives information on the imaging condition from the console 14, and outputs the information to the controller 48. The communication I/F 55 also receives the X-ray image after being subjected to the various types of processing from the frame memory 54 via the controller 48, and transmits the X-ray image to the console 14.

The controller 48 contains a timer 56. Out of the imaging condition set in the console 14, the emission time is set in the timer 56. The timer 56 starts measuring time at the instant when an emission start judging unit 57 judges that the X-ray emission has been started. The controller 48 judges that the X-ray emission is stopped when the emission time, which is determined depending on the body part to be imaged and the like, has elapsed in a time measured by the timer 56.

The controller 48 controls the operation of the emission start judging unit 57. To detect the start of the X-ray emission, the emission start judging unit 57 performs an emission start judgment, which judges whether or not the X-ray emission has been started based on a reference line image RL (see FIG. 7 and the like) outputted in the pre-emission readout operation.

Figure 6:
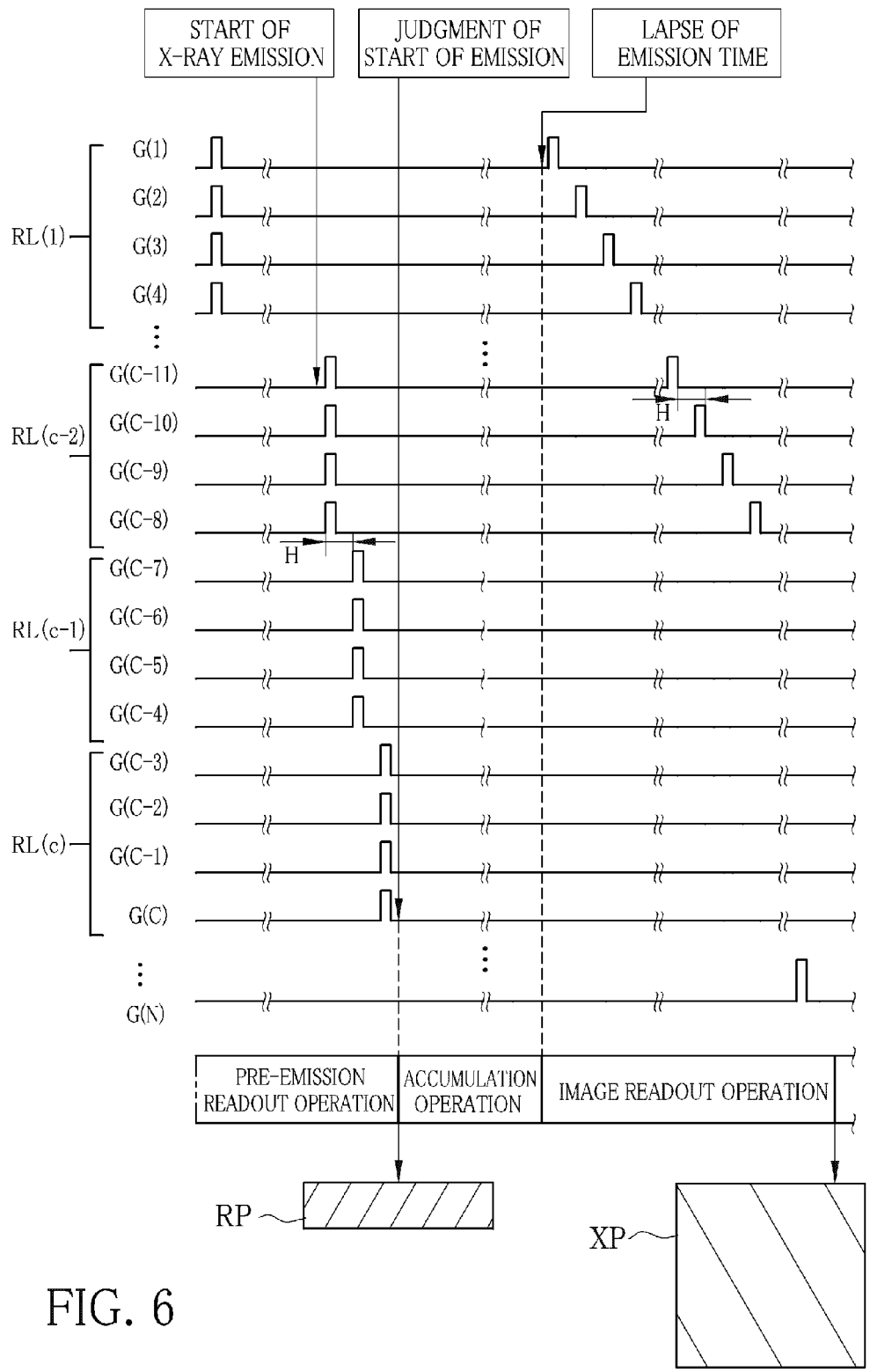
FIG. 6 is a timing chart of the operation of a panel unit.

Referring to FIG. 6, the controller 48 makes the panel unit 35 start the pre-emission readout operation, when the controller 48 receives the information on the imaging condition from the console 14 through the communication I/F 55 in a standby state before the X-ray emission. In the pre-emission readout operation, binning readout is carried out in which adjoining four pixel-rows are set as one binning pixel-row, and the gate pulse G is issued to the adjoining four pixel-rows at a time. By repeating the issue of the gate pulse G, the scan lines 44 are sequentially activated on a four-pixel-row basis and the TFTs 43 are turned on in four-pixel-row blocks, for the purpose of save time for the readout from the first pixel-row (the 1st pixel-row) to the last pixel-row (the Nth pixel-row). The electric charge is accumulated in each pixel 41 in a period of time between the binning readout of a preceding cycle of the pre-emission readout operation of one frame and the binning readout of the following cycle.

By performing the binning readout in the four-pixel-row blocks, the electric charge of the four pixels 41 adjoining in the Y direction are added in each signal line 45 and flows into the integrator 49. The controller 48 sequentially selects one of the integrators 49 using the MUX 51 and reads out output (voltage) of each integrator 49. The controller 48 converts the output of integrators 49 into digital values (pixel values S) by the A/D 52, and outputs the pixel values S to the frame memory 54 as the reference line image RL. Each pixel value S of the reference line image RL represents the sum of the pixel values of the four pixels 41 of each pixel-column.

Note that, in this specification, "RP" represents the reference line images of one frame, that is, a reference frame image. "RL" represents the reference line image of each binning pixel-row included in the reference frame image RP. "XP" represents the X-ray image of one frame. "XL" represents the X-ray image of each pixel-row included in the X-ray image XP.

As shown on a left side of FIG. 6, the binning readout of the 1st binning pixel-row, including the 1st pixel-row to the 4th pixel-row, allows obtainment of the reference line image RL(1) of one binning-row. The binning readout of the 2nd binning pixel-row, including the 5th pixel-row to the 8th pixel-row, allows obtainment of the reference line image RL(2). Likewise, the binning readout of the (C−3)th pixel-row to the Cth pixel-row allows obtainment of the reference line image RL(c). Whenever the binning readout is performed, the controller 48 inputs the amplifier reset pulse PST to the integrators 49 to reset the integrators 49.

"RL(c)" represents the reference line image of the (C−3)th pixel-row to the Cth pixel-row. "RL(c−1)" represents the reference line image of the next preceding four pixel-rows (the (C−7)th pixel-row to the (C−4)th pixel-row). "RL (c−2)" represents the reference line image of the further next preceding four pixel-rows (the (C−11)th pixel-row to the (C−8)th pixel-row). As described above, a lower-case letter "c" is used for representing the binning pixel-row of the reference line image RL. This is because the binning readout causes a mismatch between the pixel-row and the binning pixel-row of the reference line image RL. The Cth pixel-row is the pixel-row having a line defect in the X-ray image XP, while the cth binning pixel-row is the binning pixel-row corresponding to the line defect. To distinguish between the pixel-row and the binning pixel-row, the upper-case letter "C" is used for representing the pixel-row, while the lower-case letter "c" is used for representing the binning pixel-row of the reference line image RL.

The controller 48 makes the panel unit 35 perform the binning readout from the first binning pixel-row (the 1st binning pixel-row) to the last binning pixel-row (the N/4th binning pixel-row). In the pre-emission readout operation, since the one-time binning readout corresponds to the readout of the four pixel-rows, the readout of every pixel-row (the N pixel-rows) of the image capturing field 40 is repeated in a cycle of the N/4-time binning readout. In the binning readout of one cycle, the reference line images RL of the N/4 binning pixel-rows are sequentially read out at time intervals of H and recorded to the frame memory 54, and therefore, the reference frame image RP being the reference line images RL of one frame is obtained.

Figure 7:
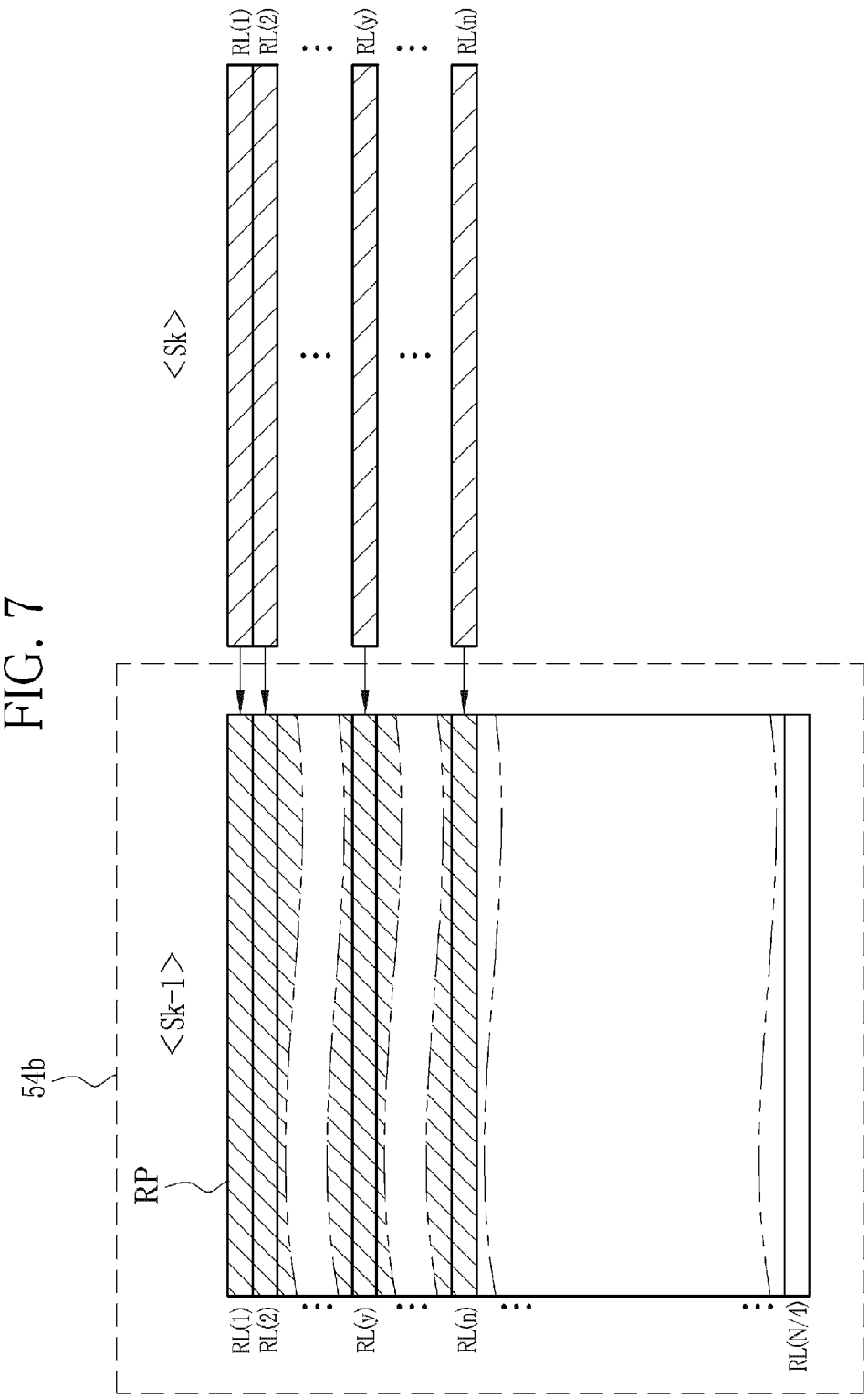
FIG. 7 is a drawing showing a second storage area of a frame memory for recording a reference frame image.

In FIG. 5, the controller 48 has a reference line image record controller (hereinafter called a RL image record controller) 48a. As shown in FIG. 7, the RL image record controller 48a controls the operation of the A/D 52 so as to record the reference frame image RP to the second storage area 54b of the frame memory 54. Whenever performing the one-time binning readout, the reference line image RL is recorded to the second storage area 54b. When the reference line image RL is obtained at a certain cycle Sk of the binning readout, the reference line image RL of the same binning pixel-row obtained in the immediately preceding cycle (Sk−1) is updated with the reference line image RL obtained in this cycle Sk. For example, when the reference line image RL(1) of the 1st binning pixel-row is obtained in the cycle Sk, the reference line image RL(1) obtained in the preceding cycle (Sk−1) is updated with the reference line image RL(1) of this cycle Sk. Thus, at that point in time when the reference line image RL(1) of the 1st binning pixel-row to the reference line image RL(n) of the nth binning pixel-row obtained in this cycle Sk have been updated, for example, the reference line images RL(1) to RL(n) of the 1st to nth binning pixel-rows are ones obtained in this cycle Sk, while the reference line images RL(n+1) to RL(N/4) of the (n+1)th to N/4th binning pixel-rows are ones obtained in the preceding cycle (Sk−1).

Figure 8:
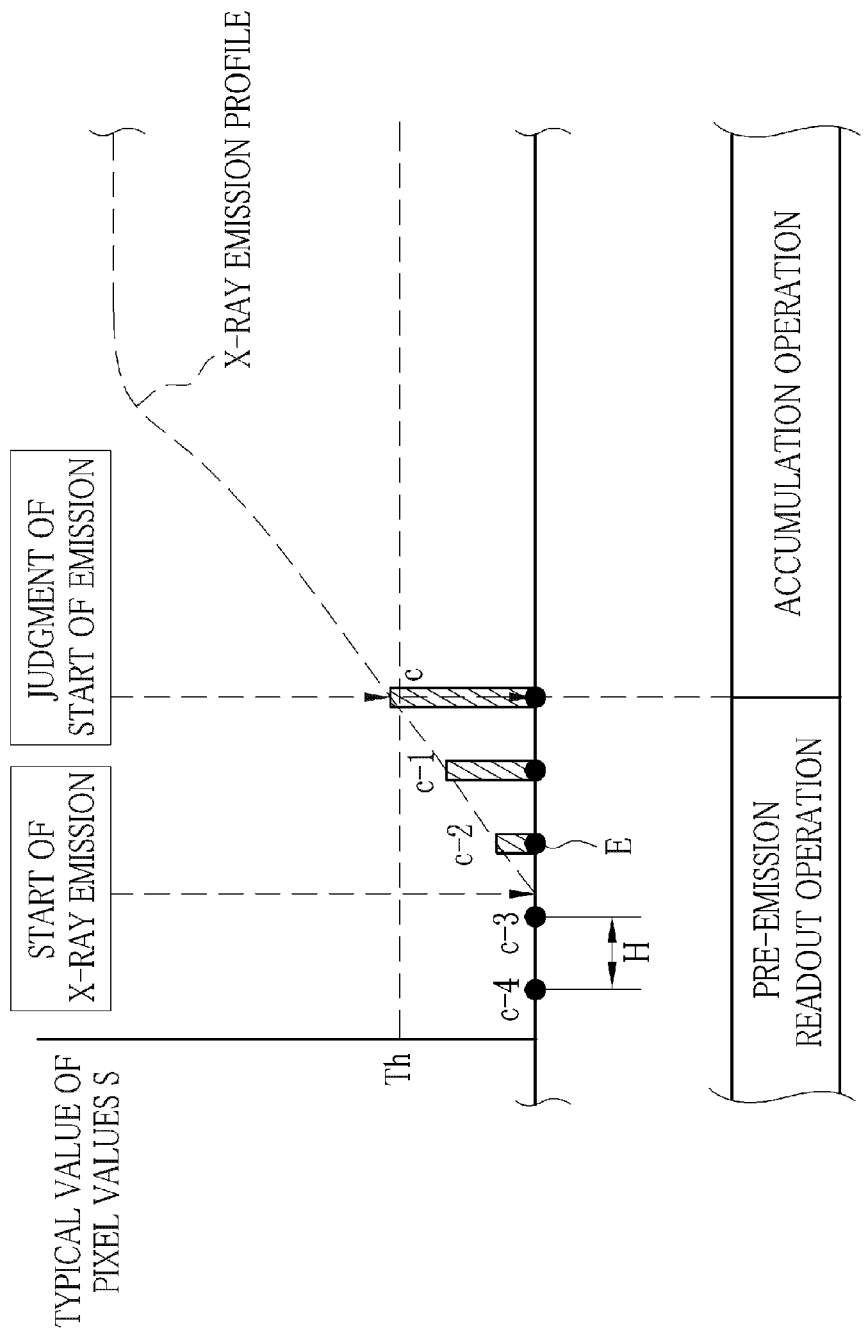
FIG. 8 is an explanatory view showing the relation among an X-ray emission profile, a pixel value S, and a judgment of an emission start.
Figure 19:
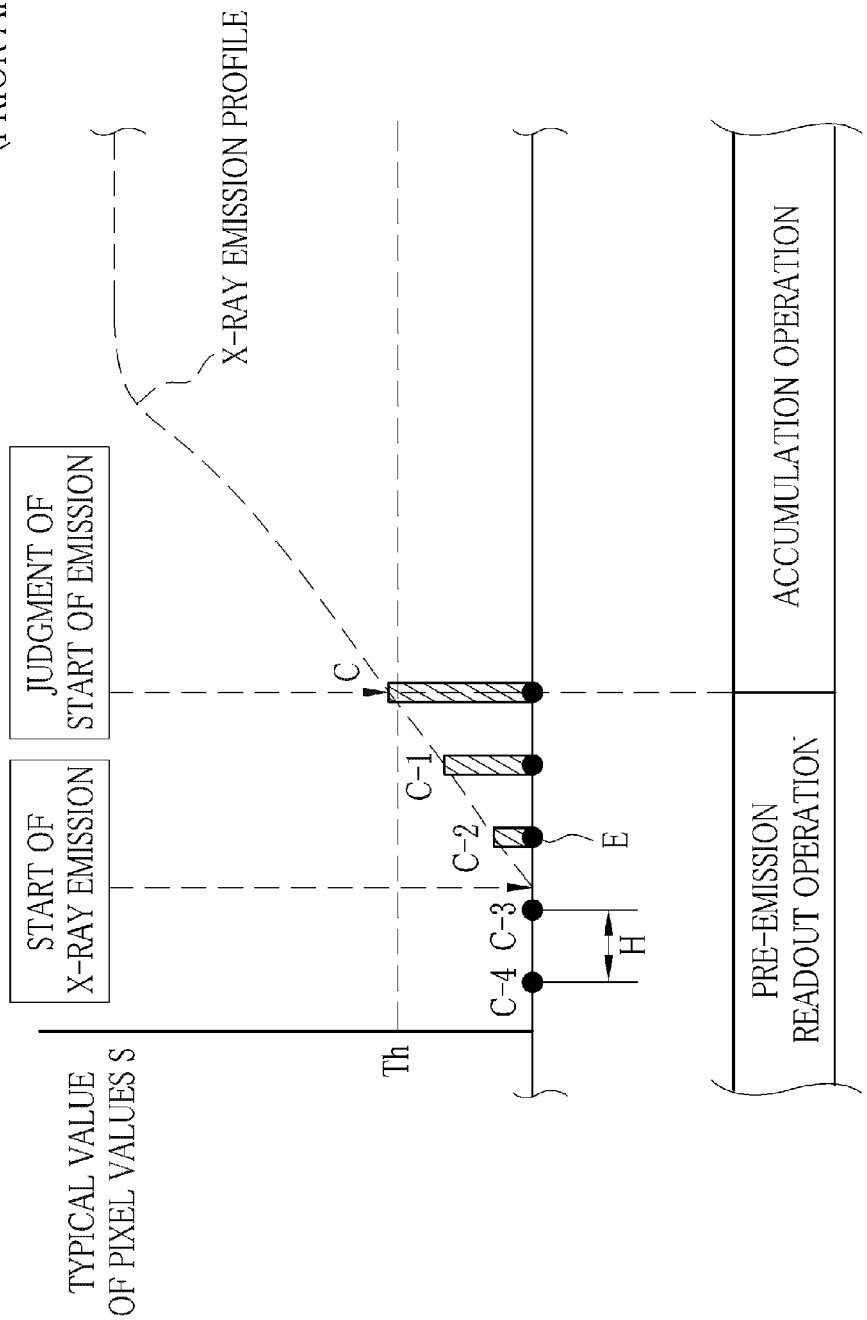
FIG. 19 is an explanatory view of the conventional relation among an X-ray emission profile, a pixel value S, and a judgment of an emission start.
Figure 20:
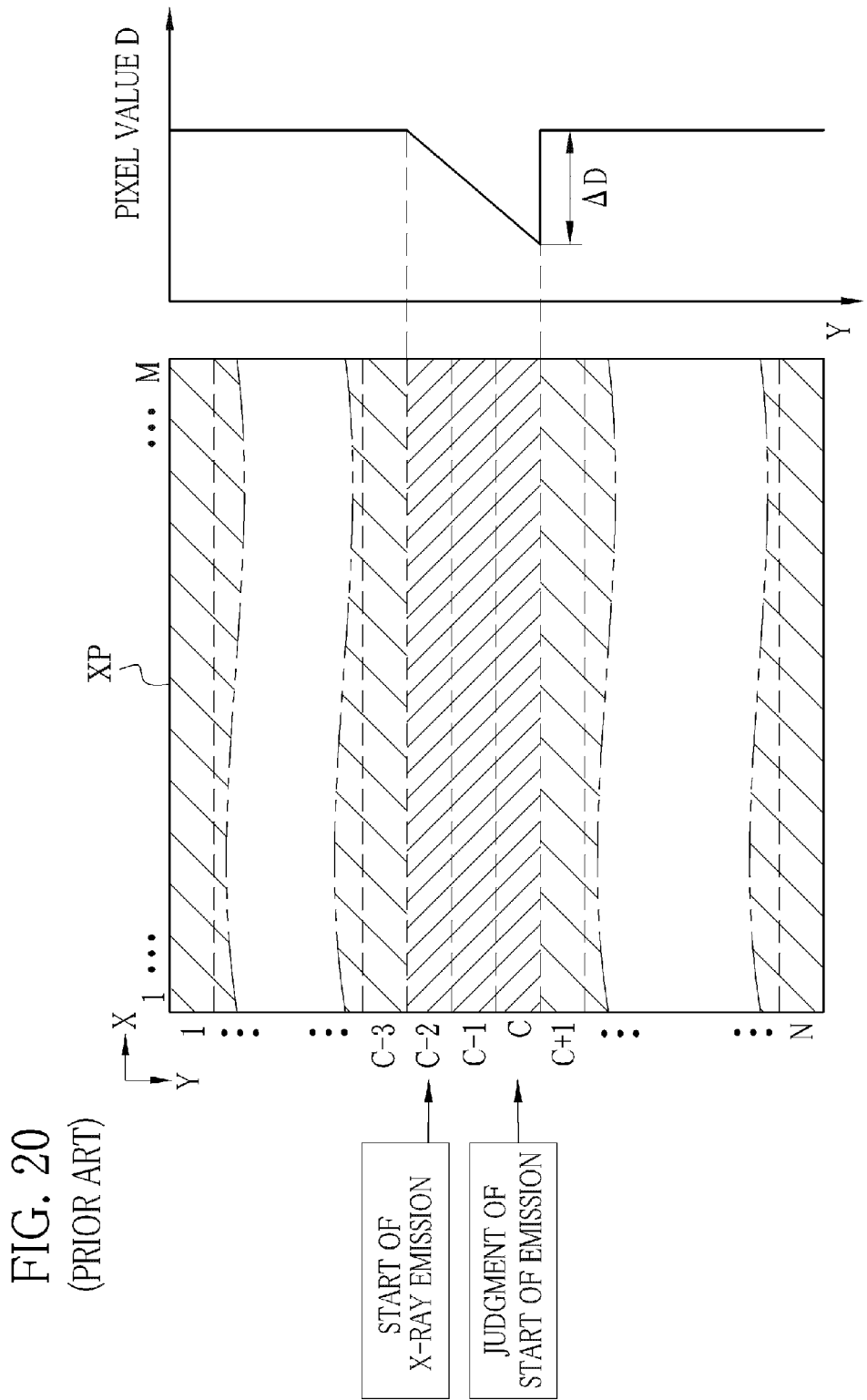
FIG. 20 is an explanatory view showing a line defect occurring in a conventional X-ray image XP and variation in a pixel value D in the Y direction.
Figure 21:
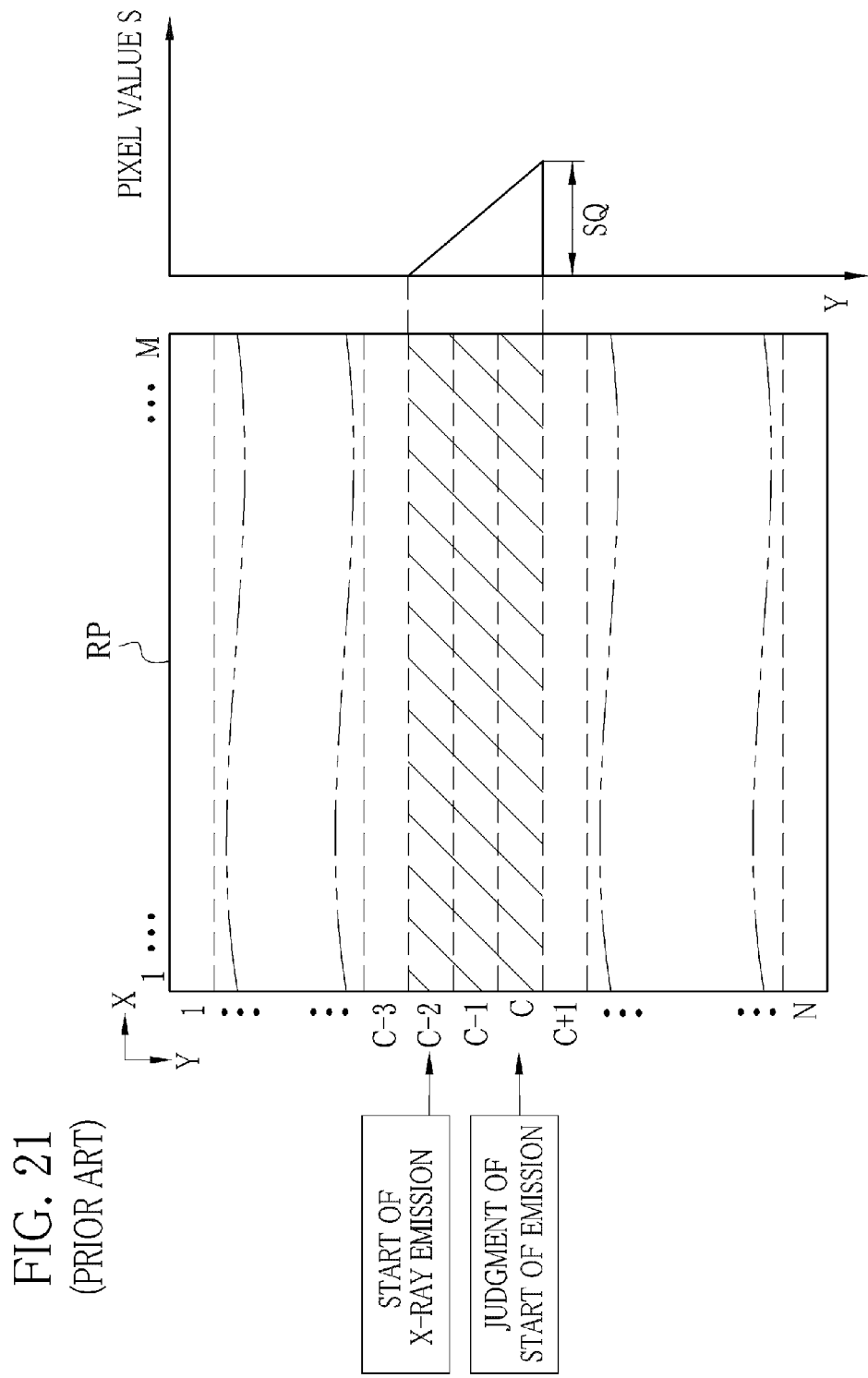
FIG. 21 is an explanatory view showing a line defect occurring in a conventional reference frame image RP and variation in a pixel value S in the Y direction.

In FIG. 8, the emission start judging unit 57 compares a typical value of the pixel values S of the reference line image RL, which is sequentially outputted at the intervals H, with a predetermined judgment threshold value Th. For the quick judgment of the emission start, a large value that has little effect of attenuation by the object is preferably used as the typical value. Thus, as the typical value to be compared with the judgment threshold value Th, a maximum value of the pixel values S of the reference line image RL is preferably used. Note that, an average or sum of the pixel values S may be used instead as the typical value. As described with referring to FIG. 19, the pixel values S of each reference line image RL outputted at each timing E are at a level of approximately zero before the start of the X-ray emission, and increased in accordance with the X-ray emission profile after the start of the X-ray emission. Then, the typical value of the pixel values S reaches a level exceeding the judgment threshold value Th. As soon as the typical value of the pixel values S exceeds the judgment threshold value Th, the emission start judging unit 57 judges that the X-ray emission has been started.

In a case where it is judged that the X-ray emission from the X-ray source 10 has been started, the emission start judging unit 57 outputs an emission start judgment signal to the controller 48. Upon receiving the emission start judgment signal from the emission start judging unit 57, the controller 48 makes the panel unit 35 stop the pre-emission readout operation and immediately shift to the accumulation operation.

In FIG. 6, the gate driver 46 is stopped in the accumulation operation. Since the TFT 43 of every pixel 41 is turned off, the pixel 41 accumulates the electric charge in accordance with the X-ray amount incident thereon. When the measured time of the timer 56 reaches the emission time set in the imaging condition, the controller 48 makes the panel unit 35 complete the accumulation operation and start the image readout operation. In the image readout operation, the gate driver 46 sequentially issues the gate pulses G to each pixel-row at the predetermined intervals H, so as to sequentially activate the scan lines on a pixel-row basis and turn on the TFTs 43 in one-pixel-row blocks. Thus, the X-ray image XP is recorded to the first storage area 54a of the frame memory 54. As described above, how to issue the gate pulses G is different between in the pre-emission readout operation and in the image readout operation. After the completion of the image readout operation, controller 48 gets the panel unit 35 back to the pre-emission readout operation in the case of continuously performing the next imaging, while stops the operation in the case of not performing the next imaging. Note that, in this embodiment, the issuing intervals H of the gate pulses G are the same between the pre-emission readout operation and the image readout operation.

FIGS. 6 to 8 show a state in which the X-ray emission is started moments before inputting the gate pulse G to the TFTs 43 of the pixels 41 of the (c−2)th binning pixel-row (the (C−11)th pixel-row to the (C−8)th pixel-row). Then, when the typical value of the pixel values S of the reference line image RL(c) obtained by the input of the gate pulse G to the TFTs 43 of the pixels 41 of the cth binning pixel-row (the (C−3)th pixel-row to the C-th pixel-row) exceeds the judgment threshold value Th, the emission start judging unit 57 judges that the X-ray emission has been started. The start of the X-ray emission is judged from the reference line image RL(c), and the pre-emission readout operation is stopped immediately after outputting the reference line image RL(c). For this reason, the reference line image RL(c) is called an immediately-preceding reference line image RL(c), as distinguished from the reference line images of the other binning pixel-rows. Upon judging the start of the X-ray emission, the controller 48 determines the coordinates of the binning pixel-row of the immediately-preceding reference line image RL(c) in the reference frame image RP, and the coordinates of the pixel-rows (the (C−3)th pixel-row to the Cth pixel-row) corresponding to the binning pixel-row of the immediately-preceding reference line image RL(c). Row coordinate information in which the coordinates of the binning pixel-row and the coordinates of the pixel-rows are related to each other is recorded to an internal memory 69 (see FIG. 11).

Figure 9:
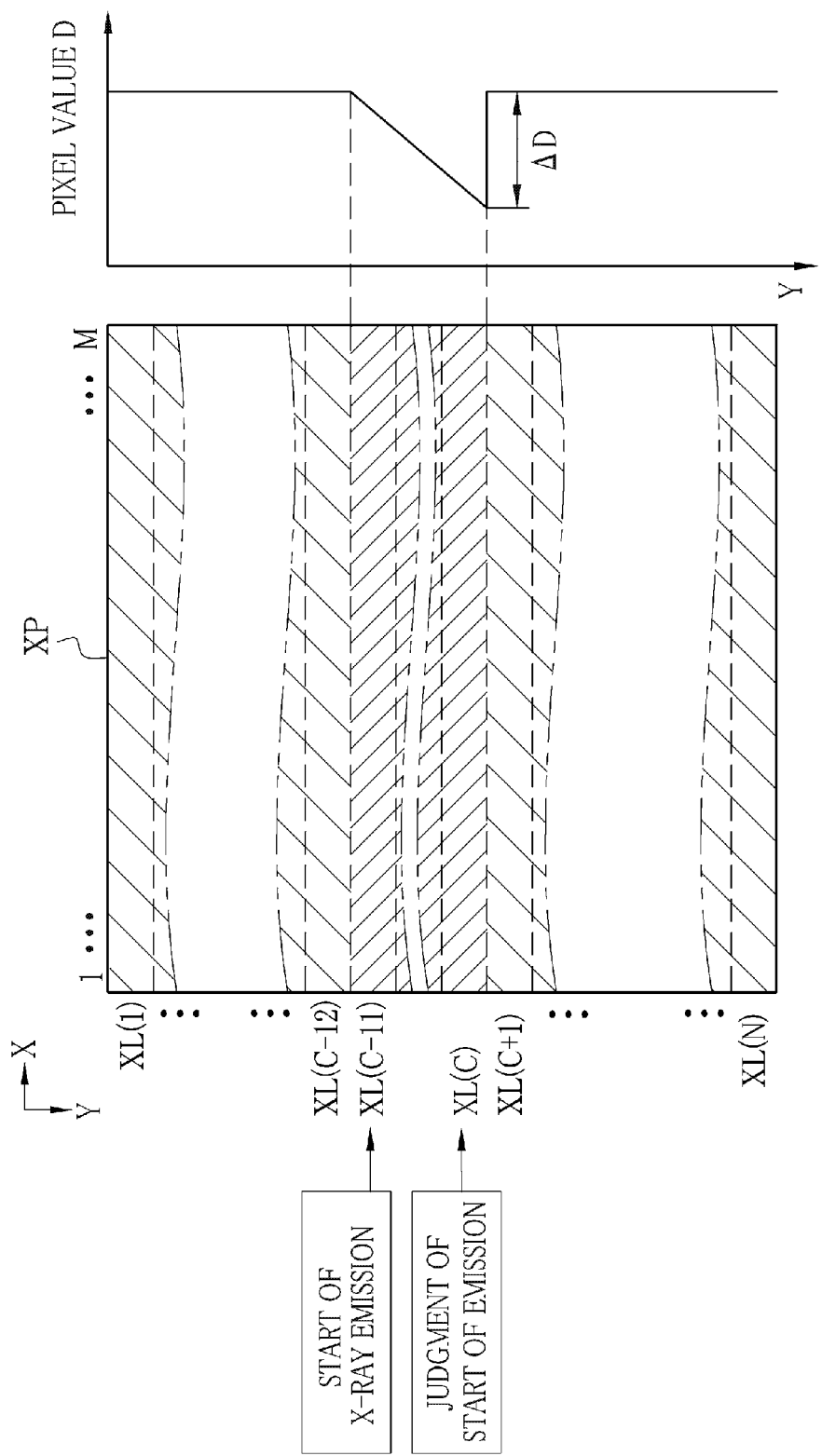
FIG. 9 is an explanatory view of a line defect occurring in an X-ray image XP and variation in a pixel value D in a Y direction.

In a case where the judgment of the emission start is delayed from the start of the X-ray emission in the pre-emission readout operation, a strip-shaped line defect occurs in the X-ray image XP, as shown in FIG. 9. In this case, the line defect occurs in twelve pixel-rows in total, including the X-ray images XL(C−11) to XL(C−8) of the four pixel-rows from the (C−11)th pixel-row to the (C−8)th pixel-row corresponding to the reference line image RL(c−2) recorded in the binning readout immediately after the start of the X-ray emission, the X-ray images XL(C−3) to XL(C) of the four pixel-rows from the (C−3)th pixel-row to the Cth pixel-row corresponding to the immediately-preceding reference line image RL(c) on which the judgment of the emission start is made, and X-ray images XL(C−7) to XL(C−4) of the four pixel-rows therebetween. According to a plot of the pixel values D of an arbitrary pixel-column X of the X-ray image XP along the Y direction, the pixel value D starts falling from around the (C−11)th pixel-row, and is the lowest at the Cth pixel-row.

Figure 10:
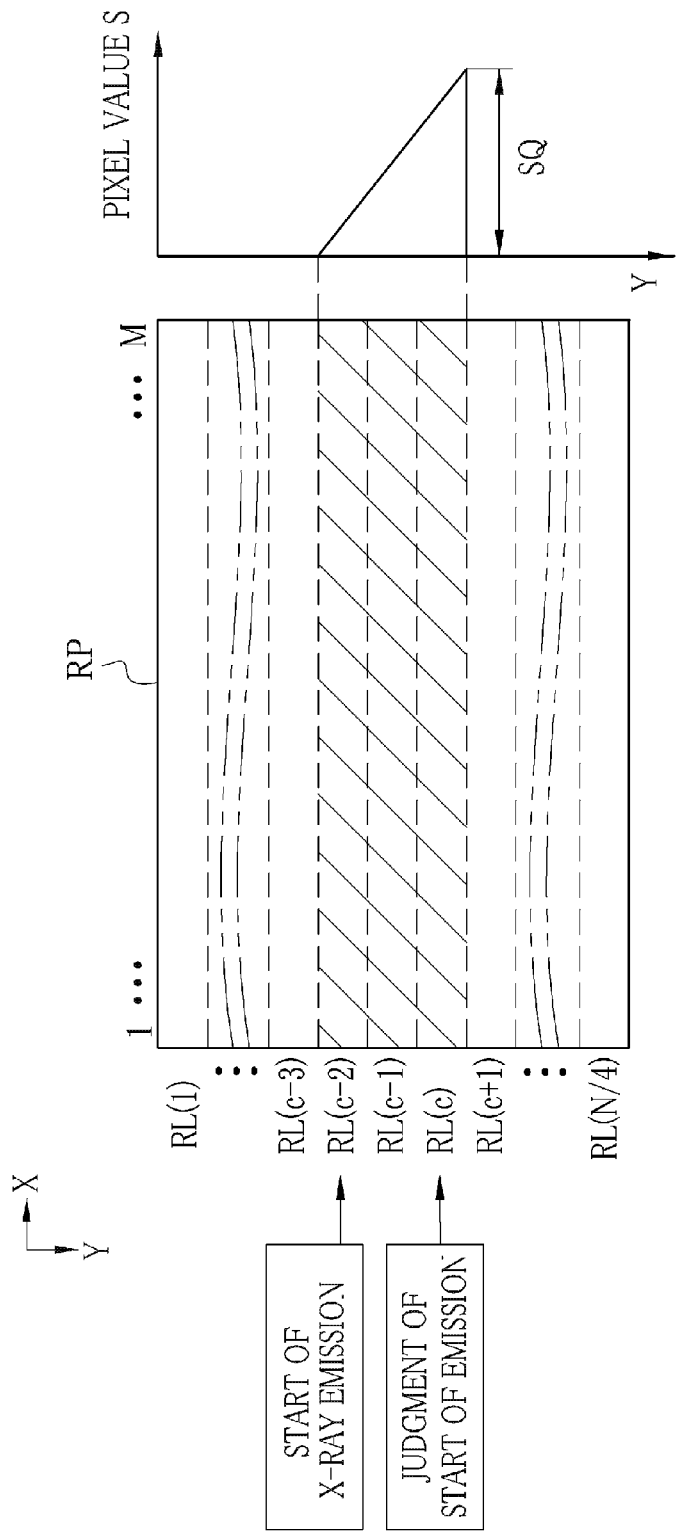
FIG. 10 is an explanatory view of a line defect occurring in a reference frame image RP and variation in a pixel value S in the Y direction.

With respect to the X-ray image XP shown in FIG. 9, in the reference frame images RP, as shown in FIG. 10, the pixel values S are increased by the electric charge in a portion corresponding to the line defect of the X-ray image XP. This increase portion of the pixel values S extends from the (c−2)th binning pixel-row at which the X-ray emission is started to the cth binning pixel-row at which the start of the X-ray emission is judged. A plot of the pixel values S of the arbitrary pixel-column X of the reference frame image RP along the Y direction is approximately zero from the 1st binning pixel-row to the (c−3)th binning pixel-row immediately before the start of the X-ray emission. The pixel values S start rising from the (c−2)th binning pixel-row, and is the highest at the cth binning pixel-row. The pixel values S of the (c+1)th binning pixel-row to the N/4th binning pixel-row are obtained from the pre-emission readout operation of the next preceding cycle before the judgment the emission start, and are approximately zero, just as with the pixel values S of the 1st binning pixel-row to the (c−3)th binning pixel-row.

Although shape is similar between a line defect portion of the X-ray image XP and the increase portion of the reference frame image RP corresponding to the line defect, the pixel values D of the X-ray image XP at the pixel-rows having the line defect are different from the pixel values S of the increase portion of the reference frame image RP corresponding to the line defect, because of performing the binning readout in the pre-emission readout operation. Also, since the number of the binning pixel-rows of the reference frame image RP is N/4, the reference frame image RP is different in image size in the pixel-column direction (Y direction) from the X-ray image XP having the N pixel-rows. Accordingly, simply adding the reference frame image RP to the X-ray image XP, as described in the Japanese Patent Laid-Open Publication No. 2011-254971, cannot correct the line defect of the X-ray image XP.

Figure 11:
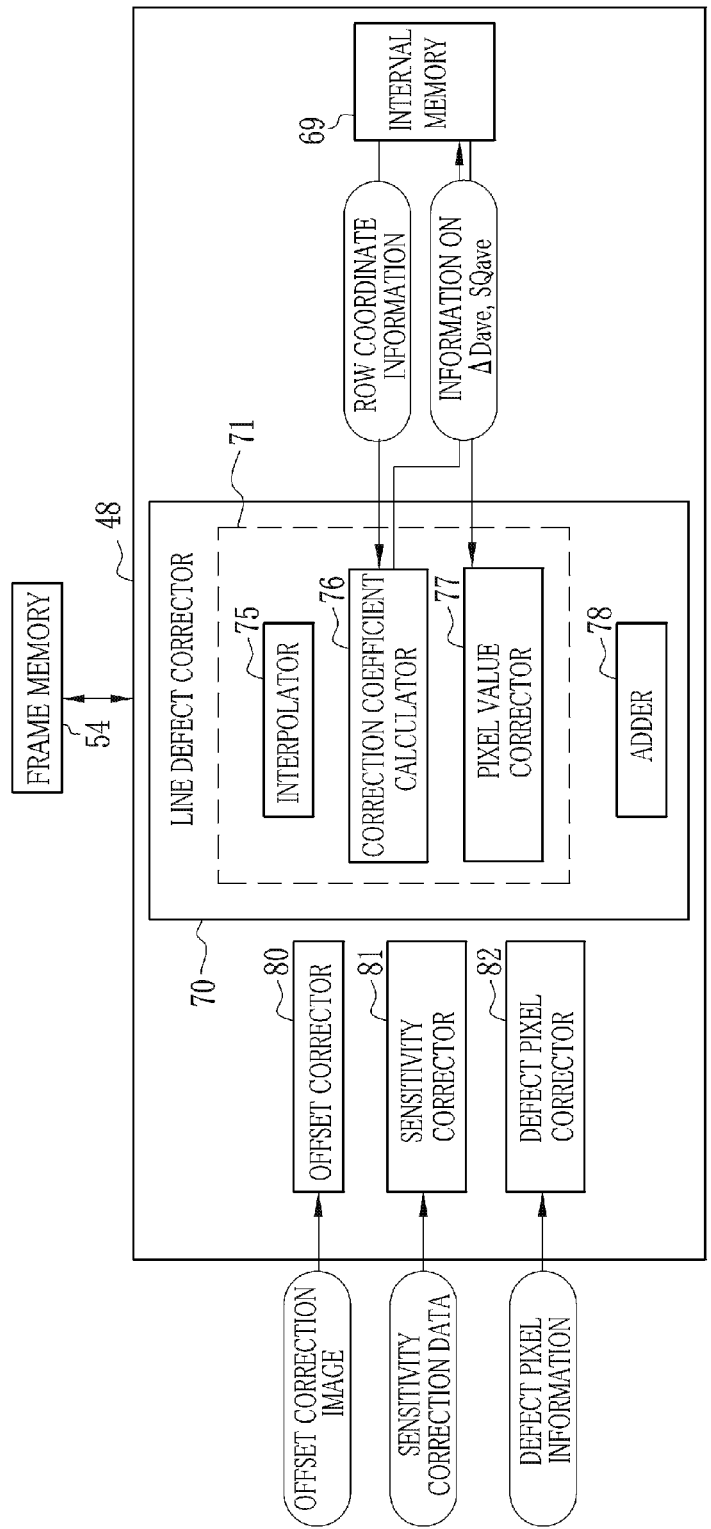
FIG. 11 is a block diagram showing various types of correctors provided in a controller.

As shown in FIG. 11, the controller 48 has a line defect corrector 70 for the X-ray image XP. The line defect corrector 70 is provided with a correction image generator 71 for producing a correction image, which is used for correcting the line defect of the X-ray image, based on the reference frame image RP.

After the completion of the image readout operation, the line defect corrector 70 reads out the X-ray image XP from the first storage area 54a and the reference frame image RP from the second storage area 54b, to perform various types of processing described later on. The line defect corrector 70 also reads out the row coordinate information, which is recorded upon the judgment of the emission start, from the internal memory 69 of the controller 48 to determine the position of the line defect.

The line defect corrector 70 is provided with an interpolator 75, a correction coefficient calculator 76, a pixel value corrector 77, and an adder 78. The interpolator 75, the correction coefficient calculator 76, and the pixel value corrector 77 compose the correction image generator 71. Since the size of the reference frame image RP in the pixel-column direction is a quarter of the image size of the X-ray image XP, the interpolator 75 applies row interpolation processing to the reference frame image RP, in order to scale up the image size in the pixel-column direction to the same image size as the X-ray image XP.

Figure 12:
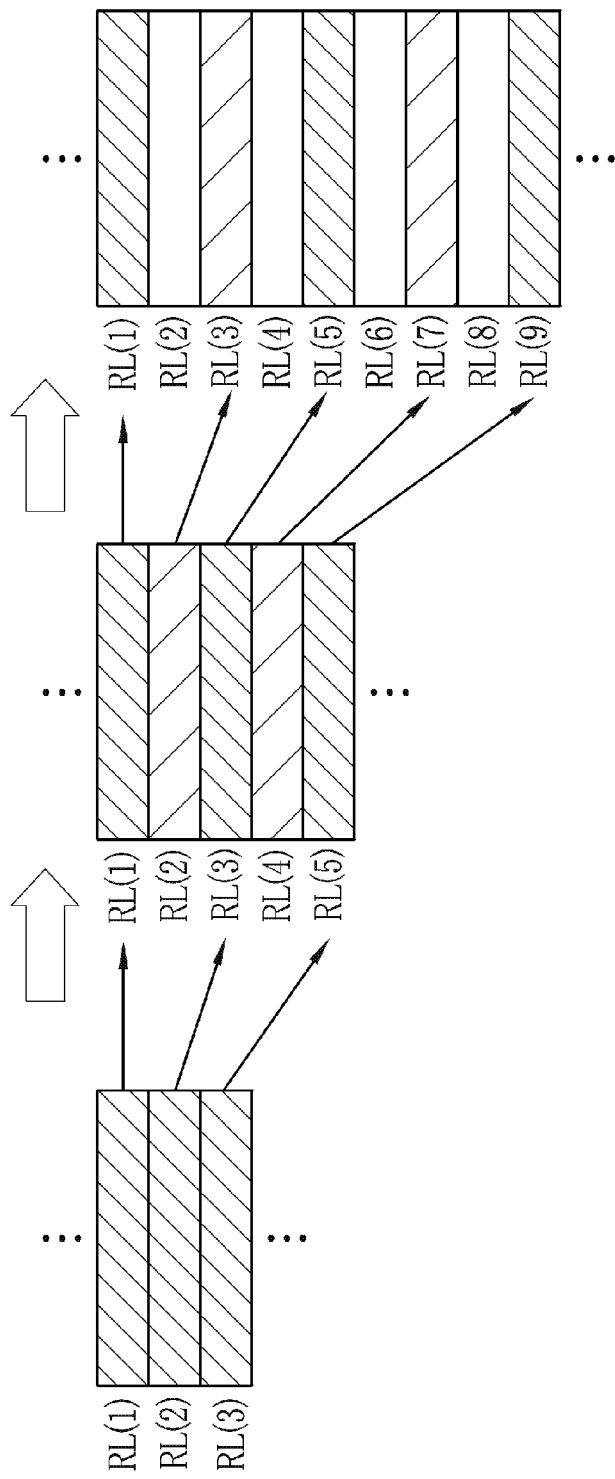
FIG. 12 is a schematic explanatory view of linear interpolation.

In the row interpolation processing, as schematically shown in FIG. 12, for example, linear interpolation is performed based on the signal values S of the reference line images RL of the adjoining two binning-rows. For example, the pixel value S of the reference line image RL(1) of the 1st binning pixel-row and the pixel value S of the reset image RL(2) of the 2nd binning pixel-row are added and divided by two, in order to obtain an interpolated reference line image RL. The correspondence of the binning pixel-rows between before and after the interpolation is shown using arrows. The reference line image RL(1) of the 1st binning pixel-row and the reference line image RL(2) of the 2nd binning pixel-row before the interpolation become the reference line image RL(1) of the 1st interpolated binning pixel-row and the reference line image RL(3) of the 3rd interpolated binning pixel-row after the interpolation, respectively. The reference line image RL obtained by the linear interpolation is inserted as the reference line image RL(2) of the 2nd interpolated binning pixel-row. Then, the linear interpolation is performed using the reference line image RL(2) of the 2nd binning pixel-row and the reference line image RL(3) of the 3rd binning pixel-row, and obtains the reference line image RL to be interpolated. The reference line image RL(3) of the 3rd binning pixel-row before the interpolation becomes the reference line image RL(5) of the 5th interpolated binning pixel-row, and the newly obtained reset image RL is interpolated as the reference line image RL(4) of the 4th interpolated binning pixel-row. By applying such row interpolation processing to every pixel-row, a reference frame image RP of twice size in the pixel-column direction can be obtained. Furthermore, applying the same row interpolation processing to the twice-sized reference frame image RP allows obtainment of a reference frame image RP that is scaled up by four times in the pixel-column direction. Note that, FIG. 12 schematically shows a part of the row interpolation processing, and the image size of the reference frame image RP in the pixel-column direction is not necessarily scaled up by twice and four times of that before the interpolation. However, the image size of the entire reference frame image RP in the pixel-column direction is scaled up by twice and four times, in actual fact. Note that, instead of the linear interpolation, spline interpolation may be used.

Since the row coordinate of the reference line image RL of each binning pixel-row is changed between before and after the interpolation, the controller 48 corrects the row coordinate information of the immediately-preceding reference line image RL(c) recorded to the internal memory 69 in accordance with the coordinates after the interpolation.

Since the reference line image RL is obtained by the binning readout of the four pixel-rows, the pixel values S of the reference line image RL is larger than the pixel values D of the X-ray image XL, which is read out on a pixel-row basis. The correction coefficient calculator 76 calculates a correction coefficient to be used for correcting the reference frame image RP, so as to convert the pixel values S of the reference line image RL into values corresponding to the pixel values D of the X-ray image XL.

The correction coefficient calculator 76 extracts the pixel values SQ of the immediately-preceding reference line image RL(c) based on the row coordinate information. Then, the correction coefficient calculator 76 calculates an average SQave=ΣS/M, which is obtained by integrating the pixel values SQ of the binning pixel-row of the immediately-preceding reference line image RL(c) and dividing the integrated value by the number M of the pixel-columns, as a typical value SQR of the pixel values SQ used in calculating the correction coefficient. The correction coefficient calculator 76 calculates a difference amount ΔD (see FIG. 9), which represents a maximum value in difference in the pixel value D between the adjoining pixel-rows, occurring in the X-ray image XP due to the line defect, based on the row coordinate information. The difference in the pixel value D is maximized at between the Cth pixel-row having the lowest pixel value D and the next (C+1)th pixel-row. More specifically, the line defect corrector 70 calculates an absolute value of the difference between the pixel value D of the X-ray image XL(C) of the Cth pixel-row and the pixel value D of the X-ray image XL(C+1) of the (C+1)th pixel-row on a column-by-column basis. Then, the line defect corrector 70 calculates an average ΔDave=ΣΔD/M by integrating the absolute values and dividing the integrated value by the number M of the pixel-columns, as a typical value ΔDR of the difference amount ΔD used in calculating the correction coefficient. The correction coefficient calculator 76 calculates ΔDave/SQave, being the ratio between SQave and ΔDave, as the correction coefficient. The correction coefficient calculator 76 outputs the obtained correction coefficient to the internal memory 69.

The pixel value corrector 77 reads out the reference frame image RP after being subjected to the row interpolation process from the second storage area 54b. The pixel value corrector 77 multiplies the pixel values S of the reference frame image RP by the correction coefficient ΔDave/SQave calculated by the correction coefficient calculator 76, to produce a correction image RPC (see FIG. 13). The correction image RPC is recorded to the second storage area 54b.

Figure 13:
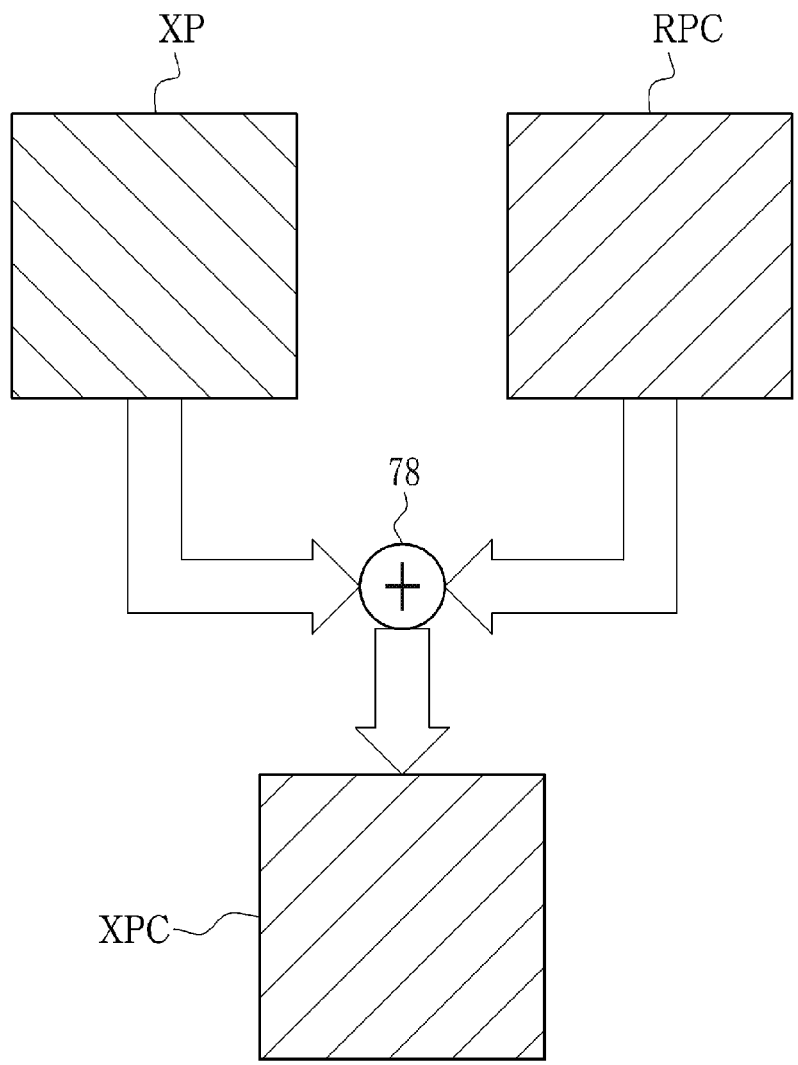
FIG. 13 is a drawing showing a state of outputting a corrected X-ray image XPC in which the linear defect is corrected by adding a correction image RPC to the X-ray image XP.

The adder 78 reads out the X-ray image XP from the first storage area 54a, and reads out the correction image RPC from the second storage area 54b. As shown in FIG. 13, the adder 78 adds the pixel value D and the pixel value S on a pixel-by-pixel basis, and produces a corrected X-ray image XPC. The adder 78 records the corrected X-ray image XPC to the first storage area 54a, instead of the X-ray image XP.

By multiplying the reference frame image RP by the correction coefficient ΔDave/SQave, the pixel value SQ of the immediately-preceding reference line image RL(c) of the corrected image RPC is equal to the difference amount ΔD in the X-ray image XP. Accordingly, the difference amount ΔD of the Cth pixel-row, which causes the line defect, disappears in the corrected X-ray image XPC, by addition of the pixel values of the correction image RPC. As for the (C−11)th pixel-row to the (C−1)th pixel-row corresponding to the line defect other than the C-th pixel-row, the addition of the pixel values of the correction image RPC makes the line defect inconspicuous in the corrected X-ray image XPC. The correction image RPC is produced based on the reference frame image RP having the rising gradient in which the falling gradient owing to the line defect is reflected, so that it is possible to make an appropriate correction to the X-ray image XP in accordance with the falling gradient due to the line defect.

In FIG. 11, the controller 48 is provided with correctors 80, 81, and 82 that apply various types of image processing including offset correct, sensitivity correction, and defect pixel correction, to the corrected X-ray image XPC. Each of the correctors 80 to 82 gets access to the first storage area 54a of the frame memory 54 and reads out the corrected X-ray image XPC. After the various types of image processing are applied to the corrected X-ray image XPC, the processed data is write back to the first storage area 54a.

The offset corrector 80 subtracts an offset correction image, which is obtained without applying the X-rays, from the corrected X-ray image XPC on a pixel-by-pixel basis, to remove a noise component caused by the dark charge contained in the electric charge. Although the dark charge is cancelled from the pixels 41 by the pre-emission readout operation, cancelling the entire dark charge of the pixels 41 requires time of one cycle, so the amount of the remaining dark charge is different from one binning pixel-row to another. The offset correction removes the remaining dark charge.

The sensitivity corrector 81, which is also called gain corrector, corrects fixed pattern noise caused by variations in the sensitivity of the photoelectric conversion element 42 among the pixels 41, variations in the output properties of the signal processing circuit 47, and the like. The defect pixel corrector 82 corrects a pixel value of a defect pixel with a pixel value of a normal pixel nearby by linear interpolation based on defect pixel information produced before shipping or in a routine checkup. The corrected X-ray image XPC after being subjected to the above image processing is transmitted to the console 14 through the communication I/F 55.

Next, a procedure of the X-ray imaging using the X-ray imaging system 2 will be described with referring to a flowchart of FIG. 14. Firstly, the object is set in an imaging position in the imaging stand 15 or the imaging table 16. The height and horizontal position of the electronic cassette 13 are adjusted in accordance with the body part to be imaged and the position of the object. The height and horizontal position of the X-ray source 10 and the size of the irradiation field are adjusted in accordance with the position of the electronic cassette 13 and the size of the body part to be imaged. Then, the imaging condition is set in the source control unit 11 and the console 14. The imaging condition set in the console 14 is transmitted to the electronic cassette 13.

After making preparation for imaging, the operator half presses the emission switch 12. Upon the half press of the emission switch 12, the warm-up command signal is issued to start warming up the X-ray source 10.

Figure 14:
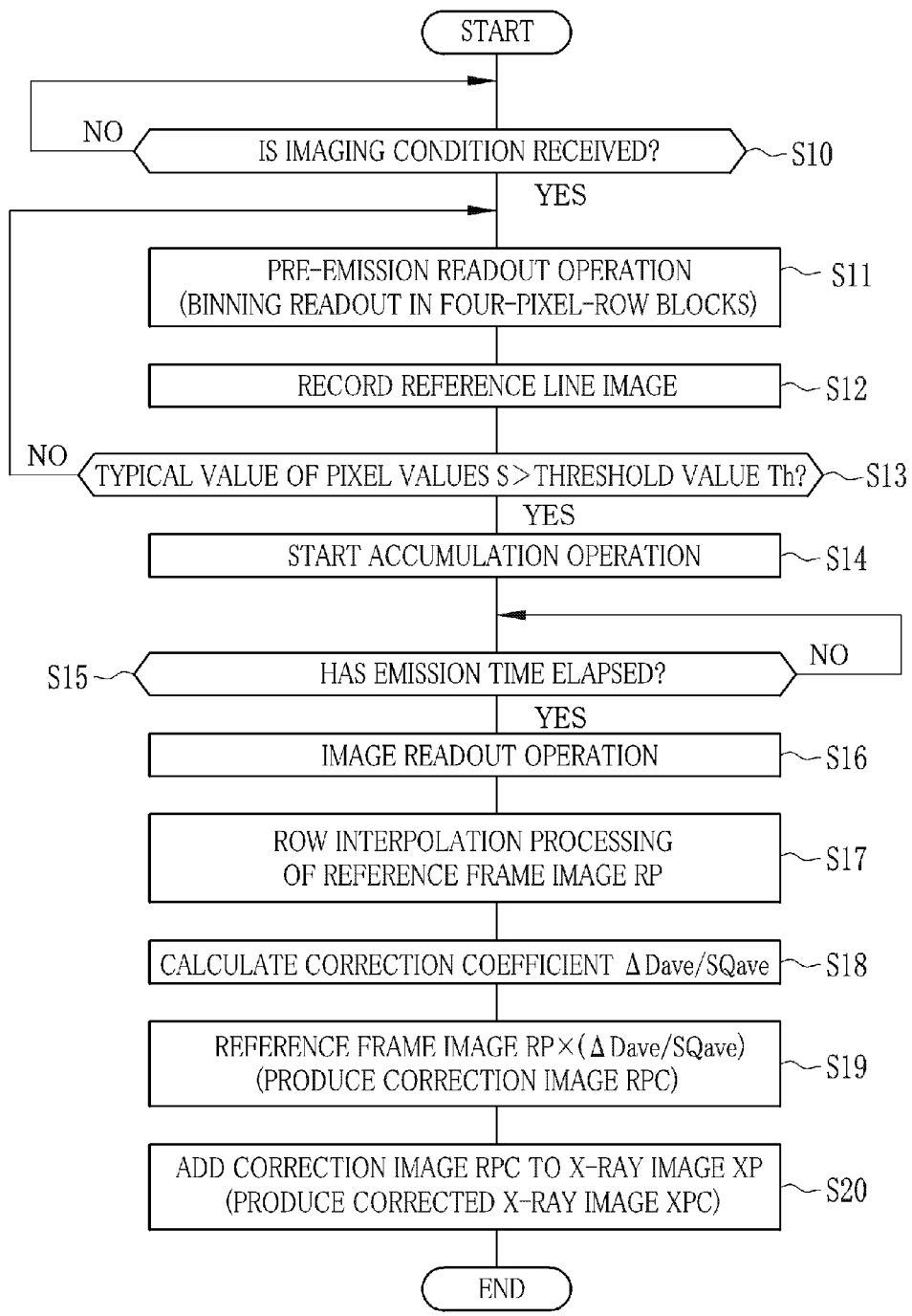
FIG. 14 is a flowchart showing the operation of the image detector.

As shown in S10 of FIG. 14, in response to receiving the imaging condition from the console 14 through the communication I/F 55 (YES in S10), the controller 48 makes the panel unit 35 start the pre-emission readout operation (S11). In the pre-emission readout operation, the binning readout is performed in four-pixel-row blocks. Thus, the electric charge accumulated in the four pixels 41 are added and discharged to the signal line 45 of each pixel-column. Whenever performing the binning readout, the RL image record controller 48a records the reference line image RL to the second storage area 54b (S12). By the binning readout of the 1st binning pixel-row to the N/4th binning pixel row, the reference frame image RP is recorded to the second storage area 54b.

Whenever the reference line image RL is recorded to the second storage area 54b, the emission start judging unit 57 reads out the reference line image RL and compares the typical value of the pixel values S of the reference line image RL with the judgment threshold value Th (S13). Before the start of the X-ray emission, the typical value of the pixel values S does not exceed the judgment threshold value Th, because the pixel values S include only output of the dark charge.

Upon the full press of the emission switch 12 by the operator, the X-ray source 10 starts emitting the X-rays. The X-ray dose per unit of time is low immediately after the start of the X-ray emission, and increased gradually. Thus, the pixel values S are low immediately after the start of the X-ray emission from the X-ray source 10. With increase in the X-ray dose, the amount of the electric charge produced in each pixel 41 is increased. Therefore, the pixel values S of the reference line image RL obtained in the binning readout are increased. After that, the typical value of the pixel values S exceeds the judgment threshold value Th. The emission start judging unit 57 judges that the X-ray emission has been started at this point in time (YES in S13).

The binning readout is performed in the pre-emission readout operation, so time required for reading out the one reference frame image RP is short. This allows reduction of the amount of the dark charge accumulated in each pixel. Also, in the case of judging the start of the X-ray emission based on the pixel values S of the reference line image RL obtained in the pre-emission readout operation, as described in the above embodiment, the pixel values S of the reference line image RL obtained by the binning readout are larger than those of a reference line image obtained by the readout in one-pixel-row blocks. Thus, the S/N ratio of the pixel value S is increased, and this facilitates making a quick and correct judgment of the emission start.

In a case where the emission start judging unit 57 judges that the X-ray emission has been started, the controller 48 turns off all the TFTs 43 and stops the pre-emission readout operation. The controller 48 makes the panel unit 35 start the accumulation operation (S14). Therefore, the timing of starting the X-ray emission and the timing of starting the accumulation operation are synchronized with each other. At the same time, the timer 56 of the controller 48 starts measuring time.

The controller 48 records to the internal memory 69 the row coordinate information, which represents the correlation between the binning pixel-row coordinates of the immediately-preceding reference line image RL(c) obtained in the binning readout immediately before stopping the pre-emission readout operation in the reference frame image RP and the pixel-row coordinates (the (C−3)th pixel-row to the Cth pixel-row) corresponding to the reference line image RL(c) in the image capturing field 40.

When the measured time of the timer 25 has reached the set emission time, the source control unit 11 stops the X-ray emission from the X-ray source 10. When the measured time of the time 56 has reached the emission time set in the imaging condition (YES in S15), the controller 48 shifts the panel unit 35 from the accumulation operation to the image readout operation (S16). In the image readout operation, the electric charge is read out on a pixel-row basis, and converted into the pixel values D by the signal processing circuit 47. The pixel values D are recorded to the first storage area 54a as the X-ray image XP.

After the image readout operation, the interpolator 75 of the correction image generator 71 applies the row interpolation processing to the reference frame image RP to scale up the image size in the pixel-column direction. Thus, the image size of the reference frame image RP becomes equal to that of the X-ray image XP (S17). The correction coefficient calculator 76 calculates the difference amount ΔD, being the absolute value of the difference between the pixel value D of the X-ray image XL(C) at which the pixel value D becomes the lowest in the line defect portion in the X-ray image XP and the pixel value D of the adjoining X-ray image XL(C+1). Then, the correction coefficient ΔDave/SQave is calculated, which is the ratio between the average ΔDave of the difference amounts ΔD and the average SQave of the pixel values SQ of the immediately-preceding reference line image RL(c) (S18). The pixel value corrector 77 multiplies each pixel value S of the reference frame image RP after being subjected to the row interpolation processing by the correction coefficient ΔDave/SQave, to produce the corrected image RPC (S19).

The adder 78 adds the correction image RPC to the X-ray image XP and produces the corrected X-ray image XPC in which the line defect is corrected (S20). Since the correction image RPC is produced based on the reference frame image RP having the increase portion in which the falling gradient corresponding to the line defect is reflected, the X-ray image XP is corrected appropriately in accordance with the falling gradient of the line defect, and thereby the corrected X-ray image XPC is produced.

Each of the correctors 80 to 82 applies the image processing including the offset correction, the sensitivity correction, and the defect correction to the corrected X-ray image XPC. The corrected X-ray image XPC after being subjected to the image processing is transmitted to the console 14 through the communication I/F 55. The corrected and processed X-ray image XPC is displayed on the display 14b and used in a diagnosis.

In the above first embodiment, the controller 48 has the RL image record controller 48a, and the controller 48 also functions as the RL image record controller 48a. However, the controller 48 and the RL image record controller 48a may be independent of each other. Likewise, the controller 48 having the line defect corrector 70 also functions as the line defect corrector 70, but the controller 48 and the line defect corrector 70 may be independent of each other. Furthermore, the line defect corrector 70 having the correction image generator 71 also functions as the correction image generator 71, but the line defect corrector 70 and the correction image generator 71 may be independent of each other.

In the above first embodiment, the one frame memory 54 is provided with the first storage area 54a for recording the X-ray image XP and the second storage area 54b for recording the reference frame image RP, but two frame memories one of which records the X-ray image XP and the other records the reference frame image RP may be provided independently. Instead of the frame memory, a line memory for recording the reference line image RL of a plurality of binning pixel-rows may be provided.

In the above first embodiment, as the typical value $\Delta DR$ of the difference amounts $\Delta D$, the average $\Delta Dave$ of the absolute values $\Delta D$ of the difference between the pixel value D of the X-ray image XL (C) corresponding to the line defect and the pixel value D of the X-ray image XL(C+1) is used. As the typical value SQR of the pixel values SQ, the average SQave of the pixel values SQ of the immediately-preceding reference line image RL(c) is used. Then, the reference frame image RP is uniformly multiplied by the correction coefficient $\Delta Dave/SQave$, being the ratio between $\Delta Dave$ and SQave. Therefore it is possible to accelerate processing speed, as compared with the case of calculating the correction coefficient $\Delta D/SQ$ on a pixel-column basis using the pixel value D of each pixel-column and the pixel value SQ of each pixel-column and performing the multiplication on a pixel-column basis. As a matter of course, in the case of giving a higher priority to accuracy, the multiplication may be performed on a pixel-column basis with the use of the correction coefficient $\Delta D/SQ$ that is calculated on a pixel-column basis using the pixel value D of each pixel-column and the pixel value SQ of each pixel-column.

Note that, a pixel value of a defect pixel is much higher than that of a normal pixel, so calculating the average SQave and the average $\Delta Dave$ from the pixel values of the pixels including the defect pixel causes deterioration in the accuracy of the correction coefficient $\Delta Dave/SQave$. Thus, it is preferable that the correction coefficient calculator 76 excludes the pixel value of the defect pixel from the pixel values SQ of the immediately-preceding reference line image RL(c) and the pixel values D of the X-ray image XL(C) of the Cth pixel-row and the X-ray image XL(C+1) of the (C+1)th pixel-row used for calculating the difference amount $\Delta D$, and then the average SQave and the average $\Delta Dave$ are obtained. As a method for excluding the pixel value of the defect pixel, there are a method of using the defect pixel information produced in shipping or routine checkup, and a method of detecting and removing a pixel value of an expected defect pixel by using a low-pass filter from the pixel values SQ of the immediately-preceding reference line image RL(c) and the pixel values D of the X-ray image XL(C) of the Cth pixel-row and the X-ray image XL(C+1) of the (C+1)th pixel-row used for calculating the difference amount $\Delta D$.

The typical value SQR of the pixel values SQ and the typical value $\Delta DR$ of the difference amounts $\Delta D$ are not limited to the averages SQave and $\Delta Dave$, as described in the above first embodiment. For example, the typical value SQR may be a median value SQC of the pixel values SQ of the immediately-preceding reference line image RL(c) (a value positioned at the center in increasing order of the pixel values SQ of the immediately-preceding reference line image RL(c)). The typical value $\Delta DR$ may be a median value $\Delta DC$ of the difference amounts $\Delta D$. Using the median values is preferable, considering the fact that the pixel value of the defect pixel, which is much higher than the pixel value of the normal pixel, is excluded by itself.

Second Embodiment

Figure 15:
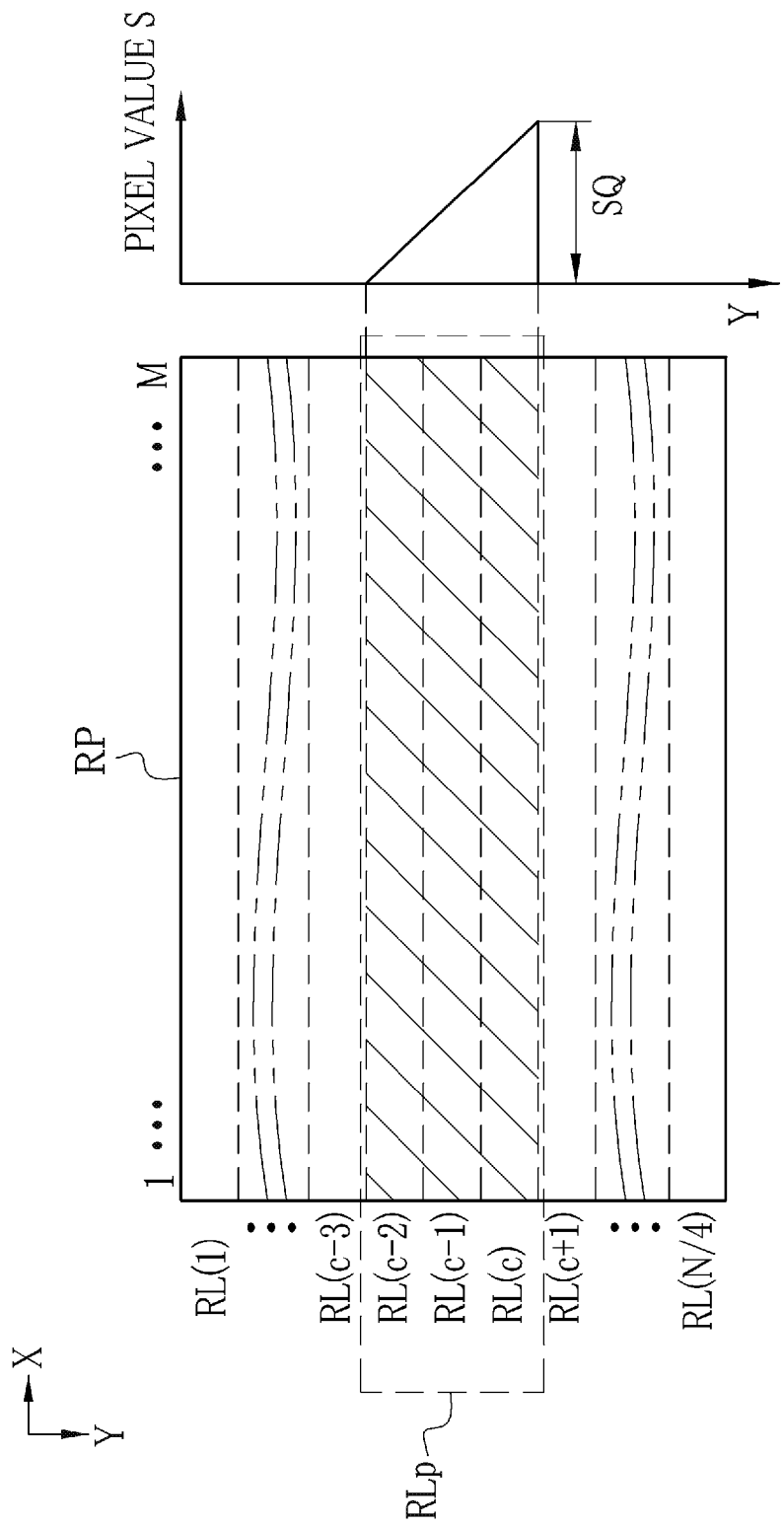
FIG. 15 is an explanatory view of the extraction of reference line images corresponding to the line defect.

In the above first embodiment, the correction image RPC is produced based on the reference frame image RP. However, the pixel values S of the reference frame image RP are approximately zero in the binning pixel-rows except for the increase portion corresponding to the line defect, and have little effect on the correction of the line defect. Thus, as shown in FIG. 15, the correction image generator 71 may extract the immediately-preceding reference line images RL(c) and the reference line images RL(c−1) and RL(c−2) of a plurality of binning pixel-rows next to the immediately-preceding reference line image RL(c), as line-defect-corresponding reference line images RLp. The correction image RPC may be produced based on the line-defect-corresponding reference line images RLp alone. This eliminates the need for multiplying the pixel values S of an approximately zero level by the correction coefficient and adding the pixel values S of the approximately zero level to the pixel values D, and hence facilitates speedup of the processing.

With respect to the immediately-preceding reference line image RL(c), for example, a predetermined number of reference line images RL next previous to the immediately-preceding reference line image RL(c) are determined as the line-defect-corresponding reference line images RLp. Since the controller 48 recognizes the time of the judgment of the emission start, the correction image generator 71 can determine the immediately-preceding reference line image RL(c) and the coordinates of the binning pixel-row of the immediately-preceding reference line image RL(c). However, the controller 48 cannot precisely recognize that at which binning pixel-row the X-ray emission is started. For this reason, the immediately-preceding reference line image RL(c) and the next previous reference line images RL of a predetermined number of binning pixel-rows are determined as the line-defect-corresponding reference line images RLp.

The correction image generator 71 applies the row interpolation processing and the calculation processing of the correction coefficient $\Delta D/SQ$ to the line-defect-corresponding reference line images RLp, to produce the correction image RPC corresponding to the line-defect-corresponding reference line images RLp. The adder 78 adds the correction image RPC to the line defect portion of the X-ray image XP.

Note that, instead of using the predetermined number of binning pixel-rows for determining the line-defect-corresponding reference line images RLp, the line-defect-corresponding reference line images RLp may be determined based on the pixel values S, for the purpose of improving accuracy. To be more specific, the pixel values S of the reference frame image RP in an arbitrary pixel-column X are scanned in the Y direction and plotted, just as with a graph on a right side of FIG. 10 or 15. According to the plot, a binning pixel-row having a pixel value S other than zero is retrieved. At this time, the binning pixel-row having the increase portion corresponding to the line defect is already known by the row coordinate information, so the pixel values S of the binning pixel-rows next previous thereto are checked. The reference line images RL of the retrieved binning pixel-rows are determined as the line-defect-corresponding reference line images RLp. Note that, one or a plurality of columns of the reference frame images RP are used for analyzing variation in the pixel value S in the Y direction. The variation in the pixel value S may be analyzed with respect to every column, and the binning pixel-rows corresponding to the line defect may be determined in each column. The line-defect-corresponding reference line images RLp may be determined in accordance with the number of times each binning pixel-row is determined to correspond to the line defect.

Depending on the timing of the judgment of the emission start, the increase portion of the reference frame image RP, corresponding to the line defect of the X-ray image XP, may extend from the N/4th binning pixel-row to the 1st binning pixel-row. Thus, in retrieving the binning pixel-row having a pixel value other than zero, the N/4th binning pixel-row of the cycle (Sk−1) is preferably checked.

Third Embodiment

In the above second embodiment, the pixel value corrector 77 uniformly multiplies the line-defect-corresponding reference line images RLp by the correction coefficient calculated by the correction coefficient calculator 76. However, the correction coefficient calculated by the correction coefficient calculator 76 is a value specific to the correction of the pixel value SQ of the immediately-preceding reference line image RL(c). Accordingly, in the case of multiplying the line-defect-corresponding reference line images RLp, which include the reference line images RL other than the immediately-preceding reference line image RL(c), by the correction coefficient calculated by the correction coefficient calculator 76, as described in the second embodiment, the line defect becomes inconspicuous but is preferably corrected more precisely.

Figure 16:
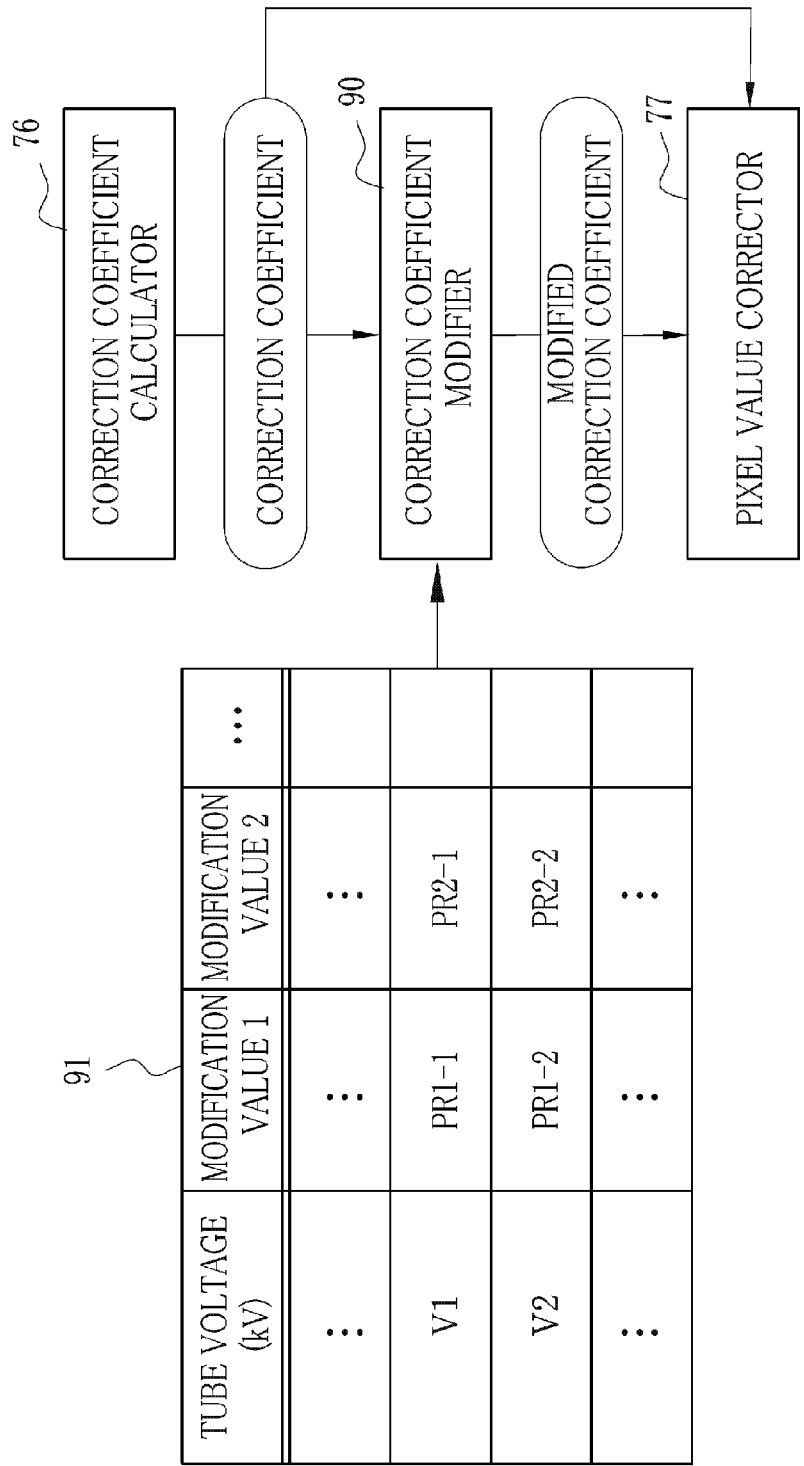
FIG. 16 is a drawing of a third embodiment having a correction coefficient proofreader.

According to this embodiment, as shown in FIG. 16, a correction coefficient modifier 90 is provided, which modifies the correction coefficient calculated by the correction coefficient calculator 76 to values (hereinafter called modified correction coefficients) for use in the line-defect-corresponding reference line images RLp.

As shown in FIG. 8, the pixel values S of the line-defect-corresponding reference line images RLp gradually increase to the pixel value SQ of the immediately-preceding reference line image RL(c) in accordance with the X-ray emission profile. The pixel values D of the X-ray image XP corresponding to the line-defect-corresponding reference line images RLp gradually decrease in accordance with the X-ray emission profile. To calculated the modified correction coefficient, the correction coefficient modifier 90 multiplies the correction coefficient calculated by the correction coefficient calculator 76 by a modification value, in which an increase rate of the pixel values S of the line-defect-corresponding reference line images RLp and a decrease rate of the pixel values D of the X-ray image XP are reflected.

More specifically, a rising gradient of the X-ray dose immediately after the start of the X-ray emission mainly depends on the tube voltage in the X-ray emission profile, so a modification value table 91, which represents the relation between the tube voltage and the modification value, is stored in advance. In the modification value table 91, the modification values corresponding to line-defect-corresponding the reference line images RLp are recorded on a tube voltage basis. For example, "modification value 1" corresponds to the reference line image RL(c−1), and "modification value 2" corresponds to the reference line image RL(c−2). The modification value is a numerical value of 0 or more and less than 1, such that the "modification value 1" is 0.9 and the "modification value 2" is 0.8. The correction coefficient modifier 90 reads out the modification values corresponding to the tube voltage, and multiplies the correction coefficient calculated by the correction coefficient calculator 76 by each of the read modification values to obtain the modified correction coefficients.

The pixel value corrector 77 multiplies the pixel value SQ of the immediately-preceding reference line image RL(c) by the correction coefficient calculated by the correction coefficient calculator 76. The pixel value corrector 77 multiplies the pixel value S of the line-defect-corresponding reference line image RLp other than the immediately-preceding reference line image RL(c) by the modified correction coefficient. Thus, the line defect correction is performed more precisely, as compared with the instance of uniformly multiplying the line-defect-corresponding reference line images RLp by the correction coefficient calculated by the correction coefficient calculator 76. Note that, as the modification value, a plurality of types of values may be prepared on a tube voltage basis, as described above, or one type of value may be used irrespective of the tube voltage.

As the correction coefficient calculated by the correction coefficient calculator 76, the reciprocal of the number of the pixel-rows composing one binning pixel-row may be used, instead of the ratio between the difference amount ΔDave and the pixel value SQave or the like, as described in the first embodiment. Taking the above first embodiment as an example, since the binning readout is carried out in four-pixel-row blocks, the correction coefficient is set at ¼. The pixel value corrector 77 multiplies the pixel value S of the reference frame image RP by the reciprocal of the number of the pixel-rows composing the binning pixel-row. However, it is preferable to use ΔD/SQ in which the actual pixel values D and S are reflected, for the sake of accuracy.

Instead of performing the row interpolation processing using the linear interpolation described in the above first embodiment, the pixel value S of each reference line image RL may be simply copied to scale up the image size of the reference frame image RP in the pixel-column direction.

In the above first embodiment, the reference frame image RP obtained in the pre-emission readout operation of a cycle of Sk is sequentially updated with the reference line images RL obtained in the pre-emission readout operation of a cycle of (Sk+1) on a binning pixel-row basis. Instead, two frame memories may be provided to record the reference frame images RP of two cycles. When a reference frame image RP is recorded to one of the frame memories, the reference frame image RP transferred to the other frame memory to empty the one frame memory. Then, the reference frame image RP of the next cycle is recorded to the empty frame memory.

According to this structure, the two reference frame images RP obtained in the cycles (Sk−1) and Sk are recorded. To determine the line-defect-corresponding reference line images RLp, it is preferable to retrieve the binning pixel-row having the pixel value S other than zero in the two reference frame images RP, in consideration of a case where the increase portion corresponding to the line defect extends to the two reference frame images RP, depending on the timing of the judgment of the emission start.

In the above first embodiment, the judgment of the emission start is performed based on the pixel values S of the reference line images RL, and thus the pixel 41 functions as an X-ray detector. Instead of this, another X-ray detector other than the pixel 41 may be provided, and the judgment of the emission start may be performed based on output of this X-ray detector. However, using the pixel as the X-ray detector, as described in the first embodiment, has a cost advantage over providing another X-ray detector.

With taking advantage of the fact that electric current flowing through the bias line, which applies the bias voltage to each pixel, is in proportional to the electric charge produced in the pixel, the X-ray dose may be detected based on the electric current flowing through the bias line connected to a specific pixel. In this case, an electric current detector for detecting the electric current of the bias line functions as the X-ray detector.

An X-ray detector other than the pixel may be provided around the image capturing field. Otherwise, an X-ray detector that is completely independent of the panel unit may be provided in the housing of the electronic cassette, or attached to the periphery of the housing.

In the above first embodiment, the offset correction is applied to the corrected X-ray image XPC. The offset correction may be applied before the line defect correction to the reference frame image RP and the X-ray image XP. Note that, a frame memory for recording a plurality of reference frame images RP is prepared, and an average of pixel values of the plurality of reference frame images RP obtained before application of the X-rays may be used as the offset correction image. The gate pulses G are issued at the same intervals H between the pre-emission readout operation and the image readout operation. However, for the purpose of enhancing responsivity in the judgment of the emission start based on the pixel values of the reference line images, the gate pulses G may be issued at shorter intervals in the pre-emission readout operation than in the image readout operation so as to shorten output intervals of the reference line images.

Fourth Embodiment

Note that, before the X-ray emission, the reference line image RL has a pixel value based on an offset of the dark charge of the pixel 41. After the X-ray emission, the reference line image RL has a pixel value based on leak current, which leaks from the pixels in the pixel-rows other than the pixel-row to be read out in the binning readout, in addition to the pixel value based on the offset and a pixel value based on the electric charge produced by the incidence of the X-rays. The pixel value based on the leak current, together with the pixel value based on the offset, becomes noise of the pixel value S, and deteriorates the accuracy of the line defect correction.

Figure 17:
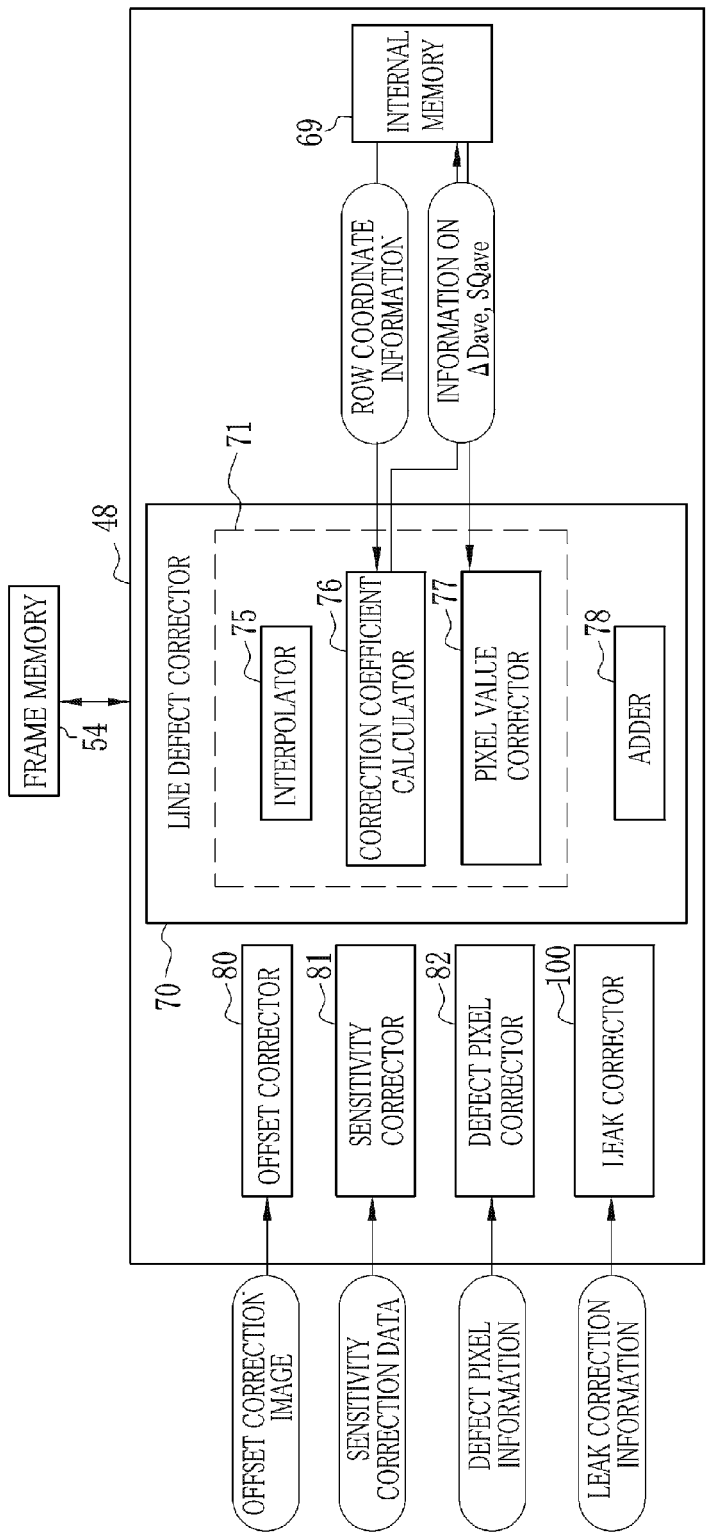
FIG. 17 is a drawing of a fourth embodiment having a leak corrector.
Figure 18:
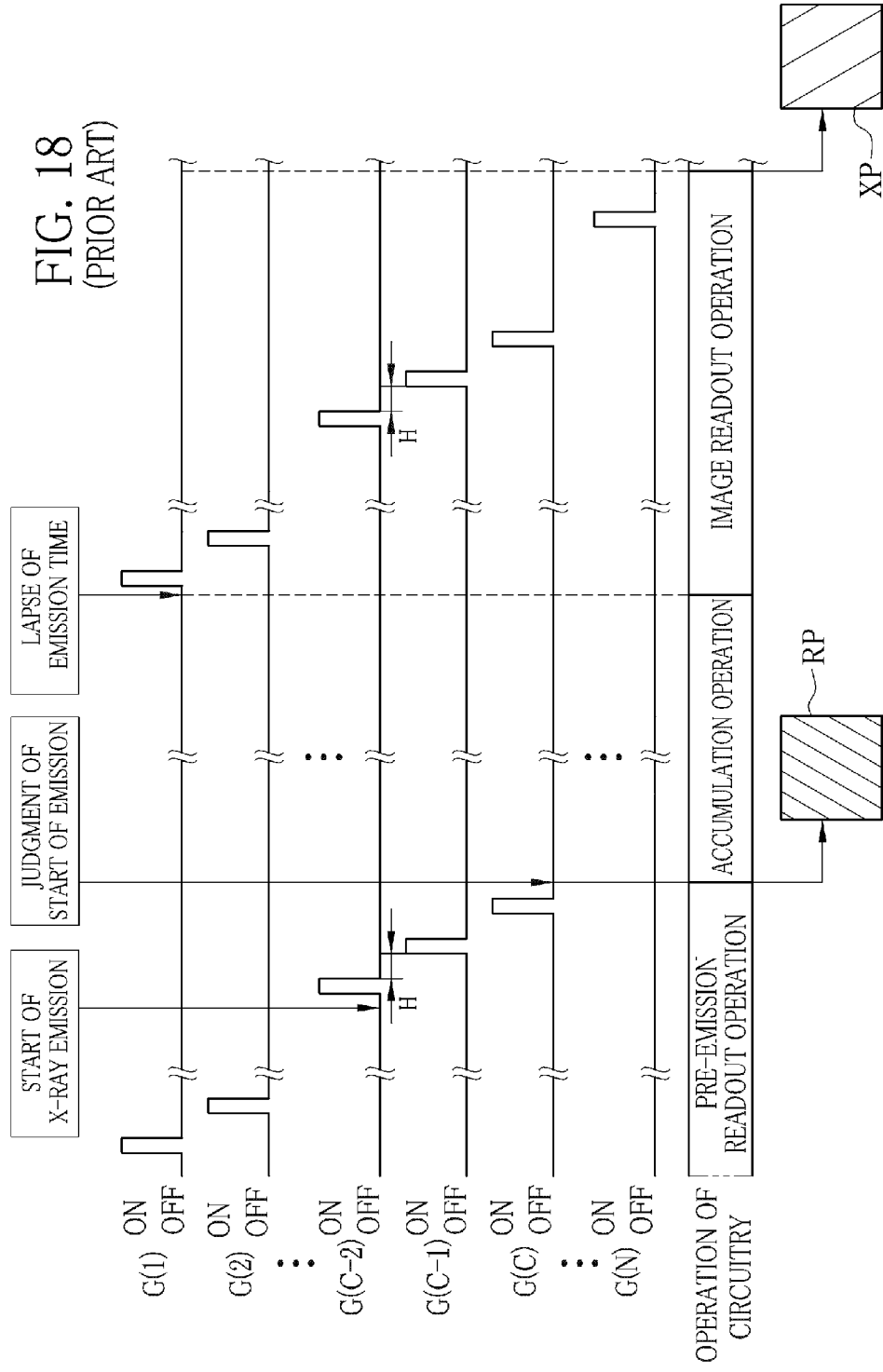
FIG. 18 is a timing chart of the operation of a conventional panel unit.

Accordingly, in this embodiment, as shown in FIG. 17, the controller 48 is provided with a leak corrector 100. Before the correction image generator 71 produces the correction image RPC, the leak corrector 100 reads out the reference frame image RP from the second storage area 54b, and performs leak correction to remove the pixel value based on the leak current from the reference frame image RP.

The level of the pixel value based on the leak current depends on the width of the irradiation field in the Y direction. Specifically speaking, the pixel value based on the leak current is relatively small, if the width of the irradiation field in the Y direction is narrow. The pixel value based on the leak current is increased with increase in the width of the irradiation field in the Y direction. In a case where the width of the irradiation field in the Y direction is equal to the width of the image capturing field 40, the pixel value based on the leak current is maximized. There is the correlation between the level of the pixel value based on the leak current and the width of the irradiation field in the Y direction. Thus, leak correction information, e.g. a data table or the like is prepared in advance that represents the correlation between the width of the irradiation field in the Y direction and the level of the pixel value based on the leak current. The leak corrector 100 reads out from the leak correction information the pixel value based on the leak current in accordance with the width of the irradiation field in the Y direction, and subtracts the read pixel value from the pixel value S of the reference frame image RP. This reduces an adverse effect of the pixel value based on the leak current on the accuracy of the line defect correction.

As a method of obtaining information on the width of the irradiation field in the Y direction, there are a method of determining the irradiation field by an image analysis of the X-ray image XP, a method of inputting irradiation field setting information of the irradiation field limiter to the console 14 and transferring the information to the electronic cassette 13, and the like. The leak corrector 100 may be provided independently of the controller 48.

The line defect corrector is provided in the controller of the electronic cassette in the above first embodiment, but may be provided in the console 14. In this case, after the completion of the image readout operation, the X-ray image XP is read out of the first storage area 54a, and the reference frame image RP is read out of the second storage area 54b. The X-ray image XP and the reference frame image RP are transmitted to the console 14 through the communication I/F 55, with being associated with the row coordinate information. Note that, in a like manner, the other correctors 80 to 82 and 100 may be provided in the console 14 so that the console 14 performs the various types of image processing.

In addition to the electronic cassette and the console, an imaging control device that performs a part of an electronic cassette control function of the console may be connected between the electronic cassette and the console. The line defect corrector described in the above embodiments may be provided in this imaging control device, or in a device other than the console 14 or the imaging control device.

The present invention may be applied to an X-ray image detecting device loaded in the imaging stand or table, instead of or in addition to the electronic cassette being the portable X-ray image detecting device. Furthermore, the present invention is applicable to a device using another type of radiation such as γ-rays, instead of the X-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation image detecting device comprising:
    a panel unit having an image capturing field for imaging a radiographic image of an object by receiving radiation emitted from a radiation source;
    a plurality of pixels arranged in said panel unit in a two-dimensional array having a plurality of pixel-rows and a pixel-column, each of said pixels producing and accumulating electric charge;
    a plurality of scan lines provided in said panel unit on a pixel-row basis, for making said pixel-row having said pixels from which said electric charge is to be read out in an ON state;
    a signal line provided in said panel unit on a pixel-column basis, for reading out said electric charge from said pixels on a pixel-column basis;
    a controller for controlling said panel unit to perform three types of operations of a pre-emission readout operation, an accumulation operation, and an image readout operation, wherein
    in said pre-emission readout operation, a plurality of adjoining said pixel-rows are set as a binning pixel-row, and binning readout of said electric charge is performed on a binning pixel-row basis sequentially from a first binning pixel-row to a last binning pixel-row and repeated from said first binning pixel-row upon reaching said last binning pixel-row, in order to obtain reference line images each having a pixel value being a sum of said electric charge of a plurality of said pixels in a same pixel-column, said accumulation operation is performed instead of said pre-emission readout operation, in a case where said radiation source starts emitting said radiation while said binning readout of said electric charge is repeated on a binning pixel-row basis, for accumulating said electric charge in said pixels in accordance with said radiation, and said image readout operation is started after completion of emission of said radiation from said radiation source, for reading out said electric charge from said pixels on a pixel-row basis and converting said electric charge to pixel values for forming said radiographic image;

a reference line image record controller for obtaining said reference line images of a plurality of said binning pixel-rows by sequentially recording said reference line images to a memory whenever performing said binning readout;

an emission start judging unit for judging start of emission of said radiation from said radiation source;

a correction image generator for producing a correction image used for correcting a strip-shape line defect occurring in a pixel-row direction of said radiographic image due to a time delay between start of emission of said radiation and a judgment of the start of emission, by scaling up an image size of said reference line images of said plurality of binning pixel-rows in a pixel-column direction and correcting said pixel values; and a line defect corrector for correcting said line defect by adding said correction image to said radiographic image.

2. The radiation image detecting device according to claim 1, wherein said correction image generator corrects said pixel value of said reference line image based on an immediately-preceding reference line image obtained immediately before stopping said pre-emission readout operation, out of said reference line images of said plurality of binning pixel-rows.

3. The radiation image detecting device according to claim 2, wherein said correction image generator includes:

a correction coefficient calculator for calculating a correction coefficient used for converting said pixel value of said reference line image to a value corresponding to a pixel value of said radiographic image; and a pixel value corrector for multiplying said pixel value of said reference line image by said correction coefficient calculated by said correction coefficient calculator.

4. The radiation image detecting device according to claim 3, wherein said correction coefficient calculator calculates a ratio $\Delta D/SQ$ as said correction coefficient, wherein SQ represents a pixel value of said immediately-preceding reference line image; and $\Delta D$ represents a difference amount being a maximum value of difference in a pixel value D of said radiographic image between adjoining two of said pixel-rows caused by said line defect.

5. The radiation image detecting device according to claim 3, wherein said correction coefficient calculator calculates a ratio $\Delta DR/SQR$ as said correction coefficient, wherein SQR represents a typical value of a pixel value SQ of said immediately-preceding reference line image; and $\Delta DR$ represents a typical value of a difference amount $\Delta D$ being a maximum value of difference in a pixel value D of said radiographic image between adjoining two of said pixel-rows caused by said line defect.

6. The radiation image detecting device according to claim 5, wherein said typical value SQR is an average SQave of said pixel values SQ; and said typical value $\Delta DR$ is an average $\Delta Dave$ of said difference amounts $\Delta D$.

7. The radiation image detecting device according to claim 6, wherein said correction coefficient calculator calculates said average SQave and said average $\Delta Dave$ with excluding a pixel value of a defect pixel from said pixel values SQ and said pixel values D that are used for calculation of said average SQave and said average $\Delta Dave$.

8. The radiation image detecting device according to claim 5, wherein said typical value SQR is a median value SQC of said pixel values SQ; and said typical value $\Delta DR$ is a median value $\Delta DC$ of said difference amounts $\Delta D$.

9. The radiation image detecting device according to claim 3, wherein said correction coefficient calculator calculates a reciprocal of a number of said pixel-rows composing said binning pixel-row, as said correction coefficient.

10. The radiation image detecting device according to claim 2, wherein said correction image generator extracts said immediately-preceding reference line image and a plurality of said reference line images next to said immediately-preceding reference line image as line-defect-corresponding reference line images, out of said reference line images of said plurality of binning pixel-rows, and produces said correction image based on said line-defect-corresponding reference line images alone.

11. The radiation image detecting device according to claim 10, wherein said pixel value corrector uniformly multiplies said pixel values of said line-defect-corresponding reference line images by said correction coefficient calculated by said correction coefficient calculator.

12. The radiation image detecting device according to claim 10, further comprising:

a correction coefficient modifier for modifying said correction coefficient calculated by said correction coefficient calculator to a correction coefficient specific to said line-defect-corresponding reference line image other than said immediately-preceding reference line image, wherein said pixel value corrector multiplies a pixel value of said immediately-preceding reference line image by said correction coefficient calculated by said correction coefficient calculator, and multiplies a pixel value of said line-defect-corresponding reference line image other than said immediately-preceding reference line image by said correction coefficient modified by said correction coefficient modifier.

13. The radiation image detecting device according to claim 1, wherein said correction image generator scales up an image size of said reference line images of said plurality of binning pixel-rows in said pixel-column direction by row interpolation processing.

14. The radiation image detecting device according to claim 13, wherein said row interpolation processing applies linear interpolation or spline interpolation between said reference line images next to each other.

15. The radiation image detecting device according to claim 1, wherein said reference line images of said plurality of binning pixel-rows coincide with said reference line images of one frame extending from said first binning pixel-row to said last binning pixel-row.

16. The radiation image detecting device according to claim 15, wherein in a case where said pre-emission readout operation of one frame extending from said first binning pixel-row to said last binning pixel-row is set as one cycle, said reference line image record controller sequentially updates said reference line images of one frame obtained in said pre-emission readout operation of an Sk-th cycle with said reference line images obtained in said pre-emission readout operation of an (Sk+1)-th cycle on a binning pixel-row basis.

17. The radiation image detecting device according to claim 1, wherein said emission start judging unit judges the start of emission of said radiation based on said reference line images.

18. The radiation image detecting device according to claim 1, further comprising:
a leak corrector for subtracting a pixel value based on leak current leaking from said pixel according to application of said radiation from a pixel value of said reference line image, before said correction image generator generates said correction image.

19. The radiation image detecting device according to claim 1, wherein said controller also functions as said reference line image record controller.

20. The radiation image detecting device according to claim 1, wherein said controller also functions as said line defect corrector.

21. The radiation image detecting device according to claim 1, wherein said line defect corrector also functions as said correction image generator.

22. An operating method of a radiation image detecting device including a panel unit having an image capturing field for imaging a radiographic image of an object by receiving radiation emitted from a radiation source; a plurality of pixels arranged in said panel unit in a two-dimensional array having a plurality of pixel-rows and a pixel-column, each of said pixels producing and accumulating electric charge; a plurality of scan lines provided in said panel unit on a pixel-row basis, for making said pixel-row having said pixels from which said electric charge is to be read out in an ON state; a signal line provided in said panel unit on a pixel-column basis, for reading out said electric charge from said pixels on a pixel-column basis; a controller for controlling said panel unit to perform three types of operations of a pre-emission readout operation, an accumulation operation for accumulating said electric charge in said pixels in accordance with said radiation, and an image readout operation for reading out said electric charge from said pixels on a pixel-row basis and converting said electric charge into pixel values for forming said radiographic image; and an emission start judging unit for judging start of emission of said radiation from said radiation source;
said operating method comprising the steps of:
A) performing said pre-emission readout operation, until said emission start judging unit judges the start of emission;
B) in said pre-emission readout operation, setting a plurality of adjoining said pixel-rows as a binning pixel-row, and performing binning readout of said electric charge on a binning pixel-row basis sequentially from a first binning pixel-row to a last binning pixel-row and repeating said binning readout from said first binning pixel-row upon reaching said last binning pixel-row, in order to obtain reference line images each having a pixel value being a sum of said electric charge of a plurality of said pixels in a same pixel-column;
C) judging the start of emission by said emission start judging unit, while said binning readout of said electric charge is repeated on a binning pixel-row basis;
D) performing said accumulation operation instead of said pre-emission readout operation, when said emission start judgment unit judges the start of emission;
E) performing said image readout operation after completion of emission of said radiation from said radiation source;
F) producing by a correction image generator a correction image used for correcting a strip-shape line defect occurring in a pixel-row direction of said radiographic image due to a time delay between the start of emission of said radiation and the judgment of the start of emission, by scaling up an image size of said reference line images of a plurality of said binning pixel-rows in a pixel-column direction and correcting said pixel values; and
G) correcting said line defect by a line defect corrector by adding said correction image to said radiographic image.

23. A radiation imaging system comprising a radiation image detecting device for detecting a radiographic image of an object by receiving radiation emitted from a radiation source, and a line defect correction device for correcting a strip-shape line defect occurring in said radiographic image,
A) said radiation image detecting device including:
a panel unit having an image capturing field for imaging said radiographic image; a plurality of pixels arranged in said panel unit in a two-dimensional array having a plurality of pixel-rows and a pixel-column, each of said pixels producing and accumulating electric charge;
a plurality of scan lines provided in said panel unit on a pixel-row basis, for making said pixel-row having said pixels from which said electric charge is to be read out in an ON state;
a signal line provided in said panel unit on a pixel-column basis, for reading out said electric charge from said pixels on a pixel-column basis;
a controller for controlling said panel unit to perform three types of operations of a pre-emission readout operation, an accumulation operation, and an image readout operation, wherein in said pre-emission readout operation, a plurality of adjoining said pixel-rows are set as a binning pixel-row, and binning readout of said electric charge is performed on a binning pixel-row basis sequentially from a first binning pixel-row to a last binning pixel-row and repeated from said first binning pixel-row upon reaching said last binning pixel-row, in order to obtain reference line images each having a pixel value being a sum of said electric charge of a plurality of said pixels in a same pixel-column,
said accumulation operation is performed instead of said pre-emission readout operation, in a case where said radiation source starts emitting said radiation while said binning readout of said electric charge is repeated on a binning pixel-row basis, for accumulating said electric charge in said pixels in accordance with said radiation, and
said image readout operation is started after completion of emission of said radiation from said radiation source, for reading out said electric charge from said pixels on a pixel-row basis and converting said electric charge to pixel values for forming said radiographic image;

a reference line image record controller for obtaining said reference line images of a plurality of said binning pixel-rows by sequentially recording said reference line images to a memory whenever performing said binning readout; and an emission start judging unit for judging start of emission of said radiation from said radiation source;

B) a line defect correction device including:

a correction image generator for producing a correction image used for correcting said line defect occurring in a pixel-row direction due to a time delay between the start of emission of said radiation and a judgment of the start of emission, by scaling up an image size of said reference line images of said plurality of binning pixel-rows in a pixel-column direction and correcting said pixel values; and a line defect corrector for correcting said line defect by adding said correction image to said radiographic image.

* * * * *